United States Patent [19]

Pelosi, Jr. et al.

[11] Patent Number: 5,691,369

[45] Date of Patent: Nov. 25, 1997

[54] CYCLIC UREAS USEFUL AS ANTIARRHYTHMIC AND ANTIFIBRILLATORY AGENTS

[75] Inventors: Stanford Salvatore Pelosi, Jr.; Chia-Nien Yu, both of Norwich, N.Y.

[73] Assignee: The Proctor & Gamble Company, Cincinnati, Ohio

[21] Appl. No.: 479,256

[22] Filed: Jun. 7, 1995

Related U.S. Application Data

[63] Continuation of Ser. No. 376,549, Jan. 23, 1995, abandoned, which is a continuation of Ser. No. 180,182, Jan. 11, 1994, abandoned, which is a continuation of Ser. No. 744,864, Aug. 14, 1991, abandoned.

[51] Int. Cl.$^6$ .................. A61K 31/415; A61K 31/505; C07D 233/02; C07D 241/04

[52] U.S. Cl. .............. 514/392; 514/235.8; 514/252; 514/255; 514/274; 514/326; 544/139; 544/315; 544/316; 544/318; 544/367; 544/370; 546/210; 548/315.7; 548/316.4; 548/322.5

[58] Field of Search .................. 514/235.8, 252, 514/274, 392, 326, 255; 544/139, 370, 315, 316, 318, 367; 548/315.7, 322.5, 316.4; 546/210

[56] References Cited

U.S. PATENT DOCUMENTS

| | | | |
|---|---|---|---|
| 3,254,075 | 5/1966 | Ebetino | 548/318 |
| 3,415,821 | 12/1968 | Davis et al. | 548/309 |
| 3,992,374 | 11/1976 | Rufer et al. | 548/318 |
| 4,393,204 | 7/1983 | Pelosi, Jr. | 548/230 |
| 4,543,359 | 9/1985 | Ellis et al. | 548/309 |
| 4,689,341 | 8/1987 | Diamond et al. | 514/399 |
| 4,705,799 | 11/1987 | Gregory | 514/376 |
| 4,707,499 | 11/1987 | Baran et al. | 514/471 |
| 4,713,832 | 12/1987 | Pascal | 377/45 |
| 4,720,580 | 1/1988 | Buzby et al. | 564/89 |
| 4,775,670 | 10/1988 | Sykes et al. | 514/210 |
| 4,870,095 | 9/1989 | Bailey | 514/406 |
| 4,876,262 | 10/1989 | Oinuma et al. | 544/256 |
| 4,963,561 | 10/1990 | Lesher et al. | 514/303 |
| 4,966,967 | 10/1990 | Lumma, Jr. et al. | 540/568 |

FOREIGN PATENT DOCUMENTS

| | | |
|---|---|---|
| 0235752 | 9/1987 | European Pat. Off. . |
| 0347733 | 12/1989 | European Pat. Off. . |
| 0431945 | 12/1991 | European Pat. Off. . |
| 8705297 | 9/1987 | WIPO . |

OTHER PUBLICATIONS

Bigger, J. T. and Hoffman, B. F., "Antiarrhythmic Drugs", Ch. 35 in Goodman and Gilman's The Basis of Pharmaceutical Therapeutics, 8th ed., ed., A. G. Gilman, pp. 840–873.

Bigger, J. T., "Antiarrhythmic Treatment: An Overview", American Journal of Cardiology, vol. 53, pp. 8B–16B, Feb. 27, 1984.

Woosley, R. L., "Antiarrhythmic Agents", in The Heart, Ch. 95, pp. 1682–1711, ed. J. W. Hurst, New York, McGraw–Hill (1990).

Woosley, R. L., "Antiarrhythmic Drugs", Annual Review. Pharmacology and Toxicology, vol. 31, pp. 427–455 (1991).

Morganroth, J. and Biggger, J. T., "Pharmacological Managment of Ventricular Arrhythmias After the Cardiac Arrhythmia Suppression Trial", American Journal of Cardiology, vol. 65, pp. 1497–1503 (1990).

Goldstein, S., "Toward a New Understanding of the Mechanism and Prevention of Sudden Death in Coronary Heart Disease", Circulation, vol. 82(1):pp. 284–288 (1990).

Echt, D. S. et al. "Mortality and Morbidity in Patients Receiving Encainide, Flecainide, or Placebo: The Cardiac Arrhythmia Suppression Trial", New England Journal of Medicine, vol. 324, pp. 781–788 (1991).

Coplen, S. E. et al. "Efficacy and Safety of Quinidine Therapy for Maintenance of Sinus Rhythm After Cardioversion: A Meta–analysis" Circulation, vol. 82, pp. 1106–1116 (1990).

Primary Examiner—Yogendra N. Gupta
Attorney, Agent, or Firm—Karen F. Clark; David L. Suter; Jacobus C. Rasser

[57] ABSTRACT

The cyclic ureas, and the pharmaceutically-acceptable salts and esters thereof, of the present invention are useful as antiarrhythmic and antifibrillatory agents and have the following general structure:

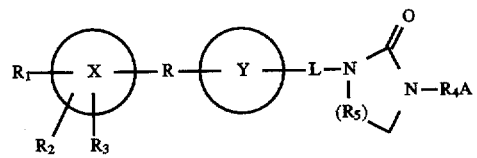

wherein X, Y, A, L, R, $R_1$, $R_2$, $R_3$, $R_4$, and $R_5$ are defined as in the Specification.

37 Claims, No Drawings

CYCLIC UREAS USEFUL AS ANTIARRHYTHMIC AND ANTIFIBRILLATORY AGENTS

This is a continuation of application Ser. No. 08/376,549, filed on Jan. 23, 1995, now abandoned, which is a continuation of application Ser. No. 08/180,182, filed on Jan. 11, 1994, now abandoned, which is a continuation of application Ser. No. 07/744,864, filed on Aug. 14, 1991, now abandoned.

BACKGROUND OF THE INVENTION

The present invention relates to novel cyclic urea compounds and pharmaceutical compounds thereof, useful in treating humans or other mammals with cardiac arrhythmia and/or cardiac fibrillation.

The novel cyclic urea compounds of the present invention are active as antifibrillatory and antiarrhythmic agents. The present compounds exhibit broad efficacy against cardiac arrhythmia and fibrillation and can be satisfactorily applied to substantially alleviate and/or prevent arrhythmia and fibrillation. In addition, said compounds exhibit a lower incidence of some of the undesirable side effects than do many conventional antiarrhythmic therapies. An additional benefit of the compounds described herein is that they exhibit both antifibrillatory and antiarrhythmic activity; most conventional therapies generally do not exhibit efficacy as antifibrillatory agents. See, e.g. Coplen, S. E. et al., "Efficacy and Safety of Quinidine Therapy for Maintenance of Sinus Rhythm after Cardioversion: A meta-analysis," *Circulation*, Vol. 82, pp. 1106–1116 (1990); and Echt, D. S. et al., "Mortality and Morbidity in Patients receiving Ecainide, Flecainide, or Placebo: The Cardiac Arrhythmia Suppression Trial", *N. Engl. J. Med.*, Vol. 324, pp. 781–788 (1991), both hereby incorporated by reference herein.

In a healthy, structurally sound heart, the precise, sequential electrical activation, then deactivation, of the entire cardiac muscle that occurs unerringly with each beat is characterized as normal cardiac rhythm. Arrhythmias are characterized as occurrences of abnormal electrical activity that can interfere with normal cardiac rhythm. The abnormal electrical activity can interfere with the initiation of, and/or the uniform spread of, the electrical wave (i.e. depolarization followed by repolarization of the cardiac muscle) that triggers the heart to contract. The disruption of the smooth, cyclical process of cardiac function associated with normal cardiac rhythm by the existence of arrhythmias is, in some instances, life-threatening.

Arrhythmias range in severity from relatively benign (consisting of asymptomatic and infrequent premature ventricular complexes [PVCs]) to life-threatening (consisting of ventricular fibrillation, and sustained ventricular tachyarrhythmia). For an excellent review of arrhythmias and an overview of antiarrhythmic therapy, see, e.g. Bigger, Thomas J., "Antiarrhythmic Treatment: An Overview", *American Journal of Cardiology*, Vol. 53, pp. 8B–16B, Feb. 27, 1984; Goldstein, S., "Toward a New Understanding of the Mechanism and Prevention of Sudden Death in Coronary Heart Disease, *Circulation*, Vol. 82(1), pp. 284–88 (1990); and Woosley, R. L., "Antiarrhythmic Drugs", *Annu. Rev. Pharmacol. Toxicol.*, Vol. 31, pp. 427–455 (1991), all hereby incorporated by reference herein. Life threatening arrhythmias are noted as a leading cause of death worldwide. For instance, it is estimated that sudden cardiac death resulting from ventricular fibrillation kills approximately 400,000–600,000 people in the United States each year. U.S. Department of Health and Human Sciences (1985) NCHS Monthly Vital Statistics Report 33:8–9.

Arrhythmias are generally classified into two types: 1) Supraventricular Arrhythmias (for example, atrial fibrillation and flutter) and 2) Ventricular Arrhythmias (for example, ventricular tachyarrhythmia and ventricular fibrillation and flutter).

Supraventricular arrhythmias are generally not life threatening. Individuals with these arrhythmias may experience a wide range of symptoms, from slight to severe intensity. These individuals may feel the physical sensation of missed beats, extra beats, and/or flutter, may occasionally feel slightly light-headed or dizzy, and may have shortness of breath and/or chest pain. Since this situation is, in fact, generally not life threatening, more aggressive therapies such as conventional antiarrhythmic drugs sometimes are not prescribed, because the side effects usually associated therewith may not be acceptable for a non-life-threatening condition. However, the novel compounds of the present invention are generally better tolerated than many of the conventional, currently available antiarrhythmics; therefore, they would likely be an acceptable therapy for individuals suffering from supraventricular arrhythmias and would substantially alleviate the discomfort these individuals experience.

Ventricular arrhythmias, on the other hand, are potentially much more serious and have been classified into three groups: 1) benign; 2) prognostically-significant (potentially lethal); and 3) life threatening (lethal). See, e.g. Morganroth, J. and Bigger, J. T., "Pharmacological management of ventricular arrhythmias after the Cardiac Arrhythmia Suppression Trial", *Amer. J. Cardiol.*, Vol. 65, pp. 1497–1503 (1990), hereby incorporated by reference herein (hereinafter Morganroth & Bigger).

Individuals with benign arrhythmias exhibit very low risk of death, cardiac scarring, and heart disease. Benign ventricular arrhythmias are relatively common and account for approximately 30% of all ventricular arrhythmias. Id. Benign arrhythmias, such as premature ventricular complexes (PVCs), pose minimal risks to individuals and rarely require antiarrhythmic therapy. However, the PVCs may be of a frequency or complexity, or are associated with sufficiently alarming symptoms, so that individuals experiencing them do not respond to reassurance that the arrhythmias and symptoms are not dangerous. They also may not respond to most conventional treatment (e.g. beta-blockers). In these cases, treatment with the novel compounds of the present invention will likely be beneficial in these individuals.

Prognostically significant arrhythmias are associated with some additional clinical presentation of cardiac disease, such as mild heart failure, ischemic symptoms, and/or cardiac scarring. It has been stated that approximately 65% of all ventricular arrhythmias are prognostically significant. See, e.g., Morganroth & Bigger, at 1497.

Patients with life threatening arrhythmias may present with syncope (sudden loss of consciousness—usually fainting—associated with insufficient brain perfusion), cardiac arrest, heart failure, and/or myocardial ischemia, in the presence of structural heart disease. Life threatening arrhythmias are relatively uncommon; probably less than 10% of the individuals suffering from arrhythmias suffer from a lethal form. Morganroth & Bigger, p. 1497. However, due to the life-threatening nature of lethal ventricular arrhythmias and the severity of symptoms associated therewith, they must be aggressively treated.

The novel compounds of the present invention are efficacious against cardiac fibrillation and supraventricular or ventricular arrhythmias. In addition, the novel compounds of the present invention exhibit less of many of the undesirable side effects which have come to be tolerated in traditional antiarrhythmic therapy, for lack of acceptable alternate therapies. For example, many current therapies cause pulmonary toxicity, cardiac depression, and neurologic effects, not specific to cardiac tissue. For an excellent discussion of the side effects associated with conventional antiarrhythmic therapies see, e.g., Bigger, J. T. and Hoffman, B. F., "Antiarrhythmic Drugs" in *Goodman and Gilman's The Basis of Pharmacological Therapeutics*, 8th edition, ed. A. G. Gilman, pp. 840–873, New York: Pergamon; and Woosley, R. L., "Antiarrhythmic Agents", in *The Heart*, ed. J. W. Hurst, pp. 1682–1711, New York: McGraw-Hill (1990), both hereby incorporated by reference herein.

In addition, the novel compounds of the present invention are readily bioavailable. This feature facilitates treatment by oral administration, and therefore greatly facilitates patient compliance. In addition, the novel compounds of the present invention are relatively inexpensive to manufacture, and they exhibit a high degree of stability in oral dosage forms.

SUMMARY OF THE INVENTION

The novel cyclic ureas of the present invention, and their pharmaceutically acceptable salts and estrs, are useful as antiarrhythmic and antifibrillatory agents and have the following general structure:

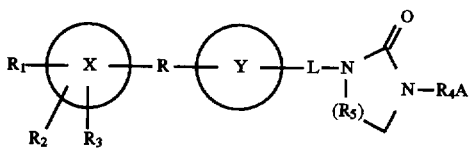

wherein (a) X is a saturated or unsaturated, 5-, 6-, or 7-membered heterocycle or carbocycle;

(b) R is selected from the group consisting of covalent bond, nil, heteroatom, carbonyl, heterocyclic ring, carbocyclic ring, alkyl, alkenyl, alkoxy, alkylamino, arylalkyl, aryloxy, acyl, acyloxy, and acylamino;

(c) Y is a substituted or unsubstituted, saturated or unsaturated, 5-, 6-, or 7-membered heterocyclic ring or carbocyclic ring, or is nil; and wherein when R is nil, X and Y are fused ring systems; and when R is a covalent bond, X and Y are ring systems linked through a covalent bond; and when Y is nil, R is a covalent bond and X is bound to L through R;

(d) $R_1$, $R_2$, and $R_3$ are independently selected from the group consisting of nil, Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino, and acyloxy;

(e) L is selected from the group consisting of alkylamino, alkenylamino, alkylimino, alkenylimino, and acylamino; wherein the nitrogen atom thereof is bound to the nitrogen atom at the 1-position of the cyclic urea moiety;

(f) $R_4$ is selected from the group consisting of alkyl, alkenyl, alkynyl, alkylacyl, and heteroalkyl;

(g) A is a substituted or unsubstituted, saturated or unsaturated, straight-chain or branched, $C_1$–$C_8$ heteroalkyl, or a substituted or unsubstituted, saturated or unsaturated heterocycle having 5-, 6-, or 7-members; and has one nitrogen atom which is adjacent to $R_4$; and (h) $R_5$ is a substituted or unsubstituted $C_1$ or $C_2$ alkyl.

THE RING SYSTEM (X-R-Y)

The novel cyclic urea compounds of the present invention are comprised of a cyclic urea moiety connected to a ring system (X-R-Y) via a linking moiety (L). The cyclic ureas have a nitrogen atom at the 3-position which is substituted with an amino-containing moiety (A) consisting of an amino group separated from the nitrogen at the 3-position of the cyclic urea moiety by a spacing group ($R_4$). The moiety represented by (X-R-Y) is a ring system moiety and consists of one or more, preferably one or two, fused or unfused, saturated or unsaturated, substituted or unsubstituted, carbocyclic rings or heterocyclic rings as defined herein. Each carbocyclic ring or heterocyclic ring contains 5, 6, or 7, preferably 5 or 6, members.

It is preferable that the ring system (X-R-Y) is polycyclic and is comprised of two, unfused rings and even more preferable that the ring represented by Y which is adjacent to the linking moiety, L, be a heterocycle, most preferably a five-membered ring which contains an oxygen heteroatom at the 1-position. In addition, when there are two rings in the ring system, it is also preferable that the heterocycle Y is covalently bound to the ring at the 5-position of the heterocycle Y and at the 1-position of the ring X, and that the heterocycle Y is bound to the L moiety at the 2-position of the heterocycle Y.

Although not preferred, it is also possible for the ring system (X-R-Y) to consist of two rings (X and Y) which are separated by an alkyl, carbonyl, or a heteroatom, most preferably oxygen (R). In addition, the ring system may be monocyclic; in this case, Y is nil and R is a covalent bond attached to L. However, when there is only one ring in the system, it is preferable that said ring be substituted with at least two, and most preferably at least three, substituents chosen from the group consisting of, but not limited to, hydroxy, methyl, chloro, methoxy, and benzoyl.

When substituted, any or all of the members of the ring system (whether monocyclic or polycyclic) may have one or more substituents, and may be substituted with Cl, F, Br, $NH_2$, $CF_3$, OH, $SO_3H$, $CH_3SO_2NH$, COOH, alkoxy, alkyl, alkoxycarbonyl, hydroxyalkyl, carboxyalkyl, aminoalkyl, acylamino or acyloxy.

THE LINKING MOIETY (L)

L is the linking moiety of the novel cyclic urea compounds of the present invention. The carbon-containing end of L is bound on to the ring system, at Y, but if Y is nil, at X; most preferably at the 2-position of the Y ring or at the 1-position of the X ring, if Y is nil. The nitrogen atom of the L moiety is bound to the nitrogen atom at the 1-position of the cyclic urea moiety. The L moiety is selected from the group consisting of, but not limited to, alkylamino, alkenylamino, alkylimino, alkenylimino, and acylamino; L is preferably an alkylimino, most preferably a $C_1$ alkylimino, CH=N.

THE CYCLIC UREA MOIETY

The cyclic urea moiety of the novel compounds of the present invention gives the novel compounds of the present invention their characteristic name. The cyclic urea moiety may be a 5- or 6-membered ring, preferably a 5-membered ring. The cyclic urea moiety is connected to the nitrogen atom of the linking moiety L at the nitrogen atom at the 1-position of the cyclic urea moiety. The cyclic urea moiety has the following structure:

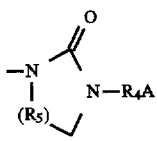

wherein $R_5$ is a $C_1$ or $C_2$ alkyl, preferably a $C_1$ alkyl. A is a heteroalkyl or a heterocyclic ring and must always contain at least one nitrogen atom which is attached to $R_4$. When A is a heteroalkyl, A may be straight-chained or branched, saturated or unsaturated, substituted or unsubstituted. When A is a heterocycle, A is a 5-, 6-, or 7-membered heterocyclic ring. Said ring may be substituted or unsubstituted, preferably substituted, and saturated or unsaturated, preferably saturated. $R_4$ is connected to the nitrogen atom at the 3-position of the cyclic urea moiety and to a nitrogen atom of A. $R_4$ is selected from the group consisting of, but not limited to alkyl, alkenyl, alkynyl, alkylacyl, and heteroalkyl.

When A is a substituted heteroalkyl, the substituents are selected from the group consisting of, but not limited to, methyl, hydroxyethyl, alkyl, aryl, heterocycle, arylalkyl, mercaptoethyl, and methanesulfonyl.

When heterocycle A has two heteroatoms and both are nitrogen, it is preferable that the nitrogen atom not adjacent to $R_4$ be substituted with substituents selected from the group consisting of, but not limited to, methyl, hydroxyethyl, alkyl, aryl, heterocycle, arylalkyl, mercaptoethyl, and methanesulfonyl. When heterocycle A has only 1 nitrogen atom, it is preferable that the heterocycle be substituted (at the position para to the nitrogen connected to $R_4$ if the heterocycle A has 6-members) with substituents selected from the group consisting of, but not limited to, hydroxyethyl, hydroxy, oxo, and methyl.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated hydrocarbon chain having 1 to 8 carbon atoms, and preferably, unless otherwise stated, from 1 to 4 carbon atoms. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Ring System" as used herein refers to the ring-containing moiety to which the cyclic urea moiety is connected through the linking moiety, L. It is denoted herein by "X-R-Y" and may be a monocyclic ring moiety, or a fused, bridged, or spiro polycyclic ring moiety, and may contain carbocycles, heterocycles, or both. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated or unsaturated or aromatic ring comprised of carbon atoms and one or more heteroatoms in the ring. Heterocyclic rings generally contain from 3 to 8, preferably 5 to 7, atoms. Unless otherwise stated, the heteroatom may be independently chosen from nitrogen, sulfur, and oxygen.

"Aryl" is an aromatic carbocyclic ring. Preferred aryl groups include, but are not limited to, phenyl, tolyl, xylyl, cumenyl, and napththyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g. —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g. —OH), and may have other substituents. Preferred hydroxyalkyl groups include, but are not limited to, hydroxyethyl, hydroxypropyl, phenylhydroxyalkyl.

"Carboxyalkyl" is a substituted hydrocarbon chain which has a carboxy substituent (e.g. —COOH), and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g. NH-alkyl-), such as dimethylamino alkyl.

"Alkylamino" is an amino moiety having one or two alkyl substituents (e.g. —N-alkyl).

"Alkenylamino" is an amino moiety having one or two alkenyl substituents (e.g. —N-alkenyl).

"Alkynylamino" is an amino moiety having one or two alkynyl substituents (e.g. —N-alkynyl).

"Alkylimino" is an imino moiety having one or two alkyl substituents (e.g. N=alkyl-).

"Arylalkyl" is an alkyl moiety substituted with an aryl group. Preferred arylalkyl groups include benzyl and phenylethyl.

"Arylamino" is an amine moiety substituted with an aryl group (e.g. —NH-aryl).

"Aryloxy" is an oxygen atom having an aryl substituent (e.g. —O-aryl).

"Acyl" or "carbonyl" is a moiety formed by removal of the hydroxy from a carboxylic acid (e.g. R—C(=O)—). Preferred alkylacyl groups include, but are not limited to, acetyl, propionyl, and butanol.

"Acyloxy" is an oxygen atom having an acyl substituent (e.g. —O-acyl); for example, —O—C(=O)-alkyl.

"Acylamino" is an amino moiety having an acyl substituent (e.g. —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

A "pharmaceutically-acceptable" salt is a catonic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred catonic salts include the alkali-metal salts (such as sodium and potassium), and alkaline earth metal salts (such as magnesium and calcium). Preferred anionic salts include the halides (such as chloride) salts.

A "biohydrolyzable ester" is an ester of the cyclic urea compounds that does not interfere with the antiarrhythmic activity of the compounds, or that is readily metabolized by a human or other mammal to yield an antiarrhythmically-active cyclic urea. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyl-oxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkylesters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, piperazinyl, morpholinyl, pyrrolidinyl, etc.), imino, thioxo, hydroxyalkyl, aryloxy, arylalkyl, and combinations thereof.

DETAILED DESCRIPTION OF THE PRESENT INVENTION

The present invention encompasses certain novel cyclic ureas, methods for their manufacture, pharmaceutical compositions thereof, and a method of treatment utilizing said novel compounds and pharmaceutical compositions thereof for cardiac arrhythmias and/or cardiac fibrillation in humans or other mammals. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response), commensurate with a reasonable benefit/risk ratio.

Novel Cyclic Urea Compounds

The compounds of this invention, herein referred to as "cyclic ureas", encompass any of a variety of cyclic urea compounds having the following general structure:

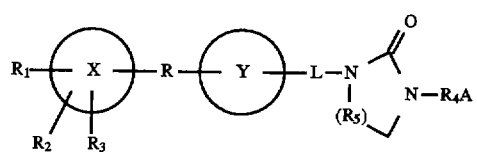

wherein (a) X is a saturated or unsaturated, 5-, 6-, or 7-membered heterocycle or carbocycle;

(b) R is selected from the group consisting of covalent bond, nil, heteroatom, carboxyl, heterocyclic ring, carbocyclic ring, alkyl, alkenyl, alkoxy, alkylamino, arylalkyl, aryloxy, acyl, acyloxy, and acylamino;

(c) Y is a substituted or unsubstituted, saturated or unsaturated, 5-, 6-, or 7-membered heterocycle or carbocycle; or is nil;

and wherein when R is nil, X and Y are fused ring systems; and when R is a covalent bond, X and Y are ring systems linked through a covalent bond; and when Y is nil, R is a covalent bond and X is bound to L through R;

(d) $R_1$, $R_2$, and $R_3$ are independently selected from the group consisting of nil, Cl, F, Br, $NH_2$, $CF_3$, OH, $SO_3H$, $CH_3SO_2NH$, $SO_2NH_2$, COOH, alkoxy, alkyl, alkoxycarbonyl, hydroxyalkyl, carboxyalkyl, aminoalkyl, acylamino and acyloxy;

(e) L is selected from the group consisting of alkylamino, alkenylamino, alkylimino, alkenylimino, and acylamino; wherein the nitrogen atom of L is bound to the nitrogen atom at the 1-position of the cyclic urea ring moiety;

(f) $R_4$ is selected from the group consisting of alkyl, alkenyl, alkynyl, alkylacyl and heteroalkyl;

(g) A is a substituted or unsubstituted, saturated or unsaturated, straight-chain or branched $C_1$–$C_8$ heteroalkyl or a substituted or unsubstituted, saturated or unsaturated heterocycle having 5-, 6-, or 7-members; and has at least one nitrogen atom which is adjacent to $R_4$, and (h) $R_5$ is a substituted or unsubstituted $C_1$ or $C_2$ alkyl;

and the pharmaceutically-acceptable salts and esters thereof.

THE RING SYSTEM (X-R-Y)

The novel cyclic urea compounds of the present invention are comprised of a cyclic urea moiety connected to a ring system (X-R-Y) via a linking moiety (L). The cyclic ureas have a nitrogen atom at the 1-position and also at the 3-position. The nitrogen atom at the 3-position is substituted with an amino-containing group (A) separated from the nitrogen atom at the 3-position of the cyclic urea moiety by a spacing group ($R_4$).

The ring system (X-R-Y) is a ring-containing moiety and consists of one or more, preferably one or two, fused or unfused, saturated or unsaturated, substituted or unsubstituted, rings as defined herein. Accordingly, the ring system may be monocyclic (Y is nil) or polycyclic (both X and Y are rings or all of X, R, and Y are rings). Each ring may be either a carbocycle or a heterocycle, and may contain 5, 6, or 7, preferably 5 or 6, members.

It is preferable that the ring system is polycyclic and is comprised of two, unfused rings. It is more preferable that the ring (Y) adjacent to the linking moiety (L) is a heterocycle, most preferably a five-membered ring which contains an oxygen atom at the 1-position. In addition, when there are two rings in the ring system, it is preferable that the heterocycle (Y) is covalently bound (through R) to the other ring (X) at the 5-position of the heterocycle Y and at the 1-position of ring X, and that heterocycle Y is bound to the carbon-containing end of the L moiety at the 2-position of the heterocycle.

Although not preferred, it is acceptable for the ring system to be a polycyclic ring system comprised of two rings (X and Y) which are separated by an alkyl, a carbonyl, or a heteroatom, preferably oxygen (R). In addition, a suitable ring system might include a polycyclic ring system comprised of two rings (X and Y) which are fused (R is nil) or three rings (X, R, and Y) which are fused. When R is a ring, it is preferably a 5- or 6-membered carbocycle or heterocycle.

A particularly suitable ring system is monocyclic, therefore, consisting of only one ring (X) which is covalently bound to the carbon-containing portion of L (R is a covalent bond and Y is nil). However, when there is only one ring in the ring system, it is preferable that the ring is a 6-membered carbocycle, which is more preferably substituted with at least two, and most preferably with at least three, substituents independently chosen from the group consisting of, but not limited to, hydroxy, methyl, chloro, methoxy, and benzoyl.

When substituted, any or all of the members of the ring system, whether monocyclic or polycyclic, may have one or more substituents. Said substituents may be independently selected from the group consisting of, and not limited to, Cl, F, Br, $NH_2$, $CF_3$, OH, $SO_3H$, $CH_3SO_2NH$, COOH, alkoxyl, alkoxycarbonyl, hydroxyalkyl, alkyl, aminoalkyl, acylamino, acyloxy, and carboxyalkyl, especially Cl, F, Br, OH and $CH_3$.

Preferred ring systems of the novel cyclic ureas include, but are not limited, for example, to monocyclic rings including, but not limited to, 2-acetoxy-5-chlorophenyl; 3-hydroxy-5-hydroxymethyl-2-methyl-4-pyridinyl; 2-thienyl; 4-pyrimidinyl; 5-methoxycarbonyl-2-furanyl; cyclohexyl; 5-chloro-2-hydroxyphenyl; 5-chloro-2-methoxyphenyl; 2-methanesulfonylaminophenyl; 3-aminophenyl; 2-methoxyphenyl; 5-ethyl-2-furanyl; 3-methoxyphenyl; 2-aminophenyl; 2-furanyl; 3,5-dimethyl-4-hydroxyphenyl; and 5-acetyloxymethyl-2-furanyl. Suitable polycyclic ring systems which consist of two unfused rings, covalently bound to one another include, for example, but are not limited to, 5-(4-carboxyphenyl)-2-furanyl; 5-(4-methanesulfonylphenyl)-2-furanyl; 5-(3,4-dimethoxyphenyl)-2-furanyl; 5-(4-methanesulfonylaminophenyl)-2-furanyl; 5-(4-bromophenyl)-2-oxazolyl; 5-(4-methoxyphenyl)-2-furanyl; 5-(1-cyclohexen-1-yl)-2-furanyl; 5-cyclohexyl-2-furanyl; 5-(3-trifluoromethylphenyl)-2-furanyl; 5-(4-methylphenyl)-2-furanyl; 2-(4-chlorophenyl)-3-furanyl; 5-(4-chlorophenyl)-2-furanyl; 5-(4-fluorophenyl)-2-furanyl. Suitable polycyclic ring systems which consists of two unfused rings each connected to one another via a heteroatom, alkyl, or other non-cyclic carbon-containing group include, for example, but are not limited to, 2-benzyloxy-5-chlorophenyl; 4-benzyloxyphenyl; 3-(4-t-butylphenyloxy)phenyl; 3-benzoyl-2,4-dichlorophenyl; 2-chloro-3-benzyloxyphenyl; 3-(4-chlorophenoxyl)phenyl. Suitable polycyclic ring systems containing two or more fused rings include, for example, but are not limited to, 1H-indol-3-yl; 2-fluorenyl; 2-naphthyl; 2-hydroxy-1-naphthyl; 2-quinolinyl; 5-chloro-2-benzofuranyl.

Preferred ring systems (X-R-Y) of the novel cyclic ureas defined herein include, but are not limited to:

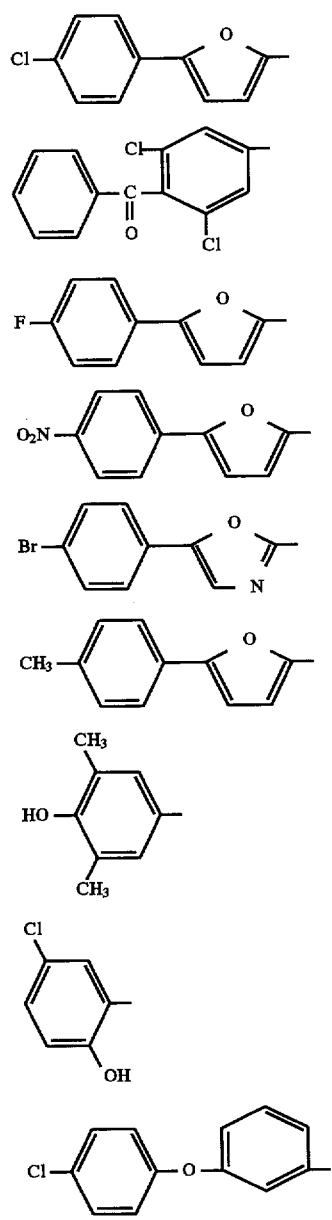

THE LINKING MOIETY (L)

L is the linking moiety of the novel cyclic urea compounds of the present invention. The carbon-containing end of L is bound to the X-R-Y ring system at Y, but if Y is nil, at X; most preferably at the 2-position of the Y ring, or at the 1-position of X, if Y is nil. The nitrogen atom of the L moiety is bound to the nitrogen atom at the 1-position of the cyclic urea moiety. The L moiety is selected from the group consisting of alkylamino, alkenylamino, alkylimino, alkenylimino, and acylamino, preferably alkylimino, most preferably a $C_1$ alkylimino, CH=N.

THE CYCLIC UREA MOIETY

The cyclic urea moiety of the novel compounds of the present invention gives the novel compounds of the present invention their characteristic name. The cyclic urea moiety may be a 5- or 6-membered ring, preferably a 5-membered ring. The cyclic urea moiety has the following structure:

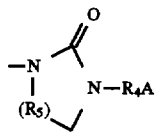

wherein $R_5$ is a $C_1$ or $C_2$ alkyl, preferably a $C_1$ alkyl. When $R_5$ is a $C_1$ alkyl, the cyclic urea is a 5-membered ring and when $R_5$ is a $C_2$ alkyl, the cyclic urea is a 6-membered ring.

A is a straight chain or branched, substituted or unsubstituted, saturated or unsaturated $C_1$–$C_8$ heteroalkyl or a substituted or unsubstituted, saturated or unsaturated 5-, 6-, or 7-, preferably 5- or 6-, membered heterocyclic ring. The A moiety, whether a heteroalkyl or a heterocycle, must have at least one nitrogen atom which must be bound to $R_4$.

When A is a substituted heteroalkyl, the substituents are selected from the group consisting of, but not limited to, methyl, hydroxyethyl, alkyl, aryl, heterocycle, arylalkyl, mercaptoethyl, and methanesulfonyl.

When A has two nitrogen atoms, it is preferable that the nitrogen atom not adjacent to $R_4$ (which in the case of a 6-membered heterocycle is para to the nitrogen atom adjacent to $R_4$) is substituted with substituents selected from the group consisting of, but not limited to, methyl, hydroxyethyl, alkyl, aryl, mercaptoethyl, methanesulfonyl, heterocycle, and arylalkyl. When heterocycle A has only one nitrogen atom, and A is a 6-membered ring, the position para to the nitrogen atom which is adjacent to $R_4$ is preferably substituted with substituents selected from the group consisting of, but not limited to, hydroxyethyl, hydroxy, oxo, and methyl.

Suitable A moieties, accordingly, may include, but are not limited to, the following: Moieties where A is a heteroalkyl include, but are not limited to, dimethylamino; diethylamino; bis-2-hydroxyethylamino; bis-[(1-methyl)ethyl]amino; N-benzyl-N-methylamino; N-(2-hydroxyethyl)-N-methylamino. Suitable A moieties where A is a heterocycle include, but are not limited to N-[(1-methyl)ethyl]-N-[2-hydroxy-2-[(4-methanesulfonylamino)phenyl]ethyl]amino; 4-phenyl-1-piperazinyl; 4-(2-hydroxyethyl)-1-piperazinyl; 4-[(1-methyl)ethyl]-1-piperazinyl; 4-[(2-methyl)propyl]-1-piperazinyl; 4-hexyl-1-piperazinyl; 4-benzyl-1-piperazinyl; 1-piperazinyl; 4-hydroxy-1-piperidinyl; 4-methyl-1-piperazinyl; 4-n-butyl-1-piperazinyl; 4-ethyl-1-piperazinyl; 3-(4-methyl-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; N-methyl-N-phenylamino; 1-imidazolyl; 4-(2-methylphenyl)-1-piperazinyl; 4-(4-methanesulfonylaminophenyl)-1-piperazinyl; N-morpholinyl; N-thiomorpholinyl; 4-oxo-1-piperidinyl; 2-(t-butoxycarbonyl)-1-pyrrolidinyl; pyrrolidinyl; 4-(4-acetylphenyl)-1-piperazinyl; hexahydro-1H-azepin-1-yl.

Preferred amine-containing (A) moieties of the novel cyclic ureas defined herein include, but are not limited to:

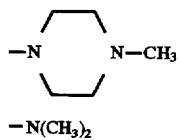

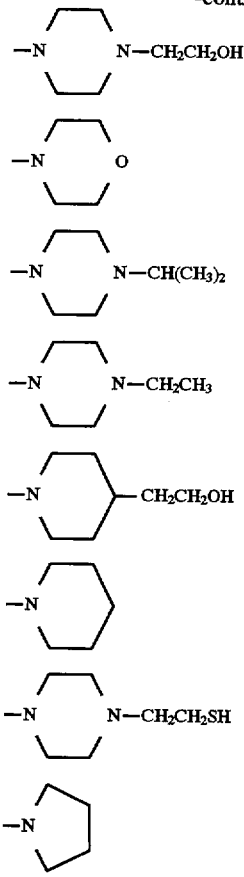

$R_4$ is connected to the nitrogen atom at the 3-position of the cyclic urea moiety and to a nitrogen atom of A. $R_4$ is selected from the group consisting of, and not limited to alkyl, alkenyl, alkynyl, alkylacyl, and heteroalkyl, especially $C_3$–$C_6$ alkyl, i.e. propyl, butyl, pentyl, and hexyl.

As stated hereinabove, the novel cyclic urea compounds of the present invention are comprised of a cyclic urea moiety connected to a ring system via a linking moiety. Accordingly, suitable compounds of the present invention include, but are not limited to, the following compounds, and the pharmaceutically-acceptable esters and salts thereof, especially the maleate and hydrochloride salts: 1-[[[5-(4-chlorophenyl)-2-furanyl]methylene]amino]-3-[3-(dimethylamino)propyl]-2-imidazolidinone; 1-[[[5-(4-chlorophenyl)-2-furanyl]methylene]amino]-3-[4-(dimethylamino)butyl]-2-imidazolidinone; 1-[[[5-(4-chlorophenyl)-2-furanyl]methylene]amino]-3-[4-(4-methyl-1-piperazinyl)butyl]-2-imidazolidinone; 1-[[[5-(4-chlorophenyl)-2-furanyl]methylene]amino]3-[2-(dimethylamino)ethyl]-2-imidazolidinone; 1-[[[3-(4-chlorophenoxy)phenyl]methylene]amino]-3-[3-(dimethylamino)propyl]-2-imidazolidinone; 1-[[5-chloro-2-benzofuranyl)methylene]amino]-3-[3-(dimethylamino) propyl]-2-imidazolidinone; 1-[[3-benzoyl-2,4-dichlorophenyl)methylene]amino]-3-[3-dimethylamino) propyl]-2-imidazolidinone; 1-[[[5-(4-chlorophenyl)-2-furanyl]methylene]amino]-3-[3-(dimethylamino)propyl] tetrahydro-2-(1H)pyrimidinone; 1-[[[5-(4-chlorophenyl)-2-furanyl]methylene]amino]-3-[4-[4-(2-hydroxyethyl)-1-piperazinyl]butyl]-2-imidazolidinone; 1-[[[5-(4-chlorophenyl)-2-furanyl]methylene]amino]-3-[3-(4-methyl-1-piperazinyl)propyl]-2-imidazolidinone; 1-[[cyclohexyl)

methylene]amino]-3-[3-(dimethylamino)propyl]-2-imidazolidinone.

Examples A–D herein illustrate how to make preferred novel cyclic urea compounds described herein.

Pharmaceutical Compositions Containing Novel Cyclic Urea Compounds

The novel cyclic urea compounds of the present invention may be administered to humans or other mammals by a variety of routes, including, but not limited to, oral dosage forms, and injections (intravenous, intramuscular, subcutaneous and intraperitoneal). Numerous other dosage forms containing the novel cyclic urea compounds of the present invention can be readily formulated by one skilled in the art utilizing the suitable pharmaceutical excipients as defined below. For considerations of patient compliance, oral dosage forms are generally most preferred.

The term "pharmaceutical composition" as used herein means a combination comprised of a safe and effective amount of the cyclic urea compound active ingredient, or mixture thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular cyclic urea compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual, either by intravenous, intramuscular, subcutaneous or intraperitoneal injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere with the activity of the particular active ingredient selected;

(c) the type of the excipient, and the concomitant desirable thickness and permeability (swelling properties) of said excipient;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different cyclic urea active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically acceptable excipients include, but are not limited to, resins, fillers, binders, lubricants, solvents, glidants, disintegrants cosolvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions described herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical compositions of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol, benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Accordingly, the pharmaceutical compositions of the present invention include from 15–95% of a cyclic urea compound active ingredient, or mixtures thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein in Examples E–J. It is well within the capabilities of one skilled in the art to vary the non-limiting examples described herein to achieve a broad range of pharmaceutical compositions.

Method of Treating Arrhythmias with the Novel Cyclic Urea Compounds

The novel compounds of the present invention are efficacious in treating humans or other mammals afflicted with supraventricular arrhythmias and ventricular arrhythmias, and/or cardiac fibrillation. As stated hereinabove, except in rare cases, supraventricular arrhythmias are not deemed to be life threatening and are generally not aggressively treated with conventional antiarrhythmic drugs due to their undesirable side effects. Accordingly, this type of arrhythmia is usually not aggressively treated to merely relieve symptoms which are characterized as mild to severe. However, the novel compounds of the present invention are generally well tolerated and generally exhibit less of the undesirable side effects than many conventional antiarrhythmic drugs and, accordingly, may well be an acceptable therapy to alleviate the physical and emotional symptoms suffered by individuals exhibiting supraventricular arrhythmias who are, in fact, experiencing discomfort, even though not in a life-threatening situation.

As stated hereinabove, the novel cyclic urea compounds of the present invention are also effective in treating ventricular arrhythmias, which are, as a rule, much more serious than atrial arrhythmias and, accordingly, require aggressive therapy. Because of the potential seriousness of some ventricular arrhythmias, many patient-type classifications have arisen.

Individuals suffering from benign ventricular arrhythmias are, from a philosophical standpoint of whether-to-treat, similar to those individuals experiencing supraventricular arrhythmias. These individuals do not have heart disease and may experience syncope, dizziness, and palpitations, and often suffer from a certain amount of emotional distress stemming from uncertainty caused by their physical symptoms. These individuals generally suffer from PVCs which are, for the most part, physically harmless, but understandably give rise to some degree of anxiety. The novel cyclic urea compounds of the present invention generally exhibit less of the undesirable side effects which may have made the use of many conventional antiarrhythmic therapies, heretofore reserved for more serious and/or life-threatening disease states, undesirable. However, these individuals would likely benefit from therapy which is generally better tolerated.

Another class of individuals who may benefit from therapy utilizing the novel cyclic urea compounds of the present invention are those individuals who are characterized as having "prognostically-significant" arrhythmias. These individuals generally have suffered a myocardial infarction and may have PVCs and/or episodes of non-sustained ventricular tachyarrhythmia, either symptomatic and asymptomatic. They do not exhibit the same degree of immediate, urgent life-threatening symptoms as do those individuals described hereinbelow, and are not, by conventional characterization, in danger of immediate- or near-death. They are, however, at a significantly greater risk of sudden death than the general populace, and, accordingly, would be at a lessened risk of cardiac failure with therapy from the novel compounds of the present invention. See Morganroth & Bigger at 1498.

Other individuals exist who continually exhibit life-threatening arrhythmias and are in danger of immediate-or-near death. In these individuals, there is generally exhibited sustained ventricular tachyarrhythmia or ventricular fibrillation. The ventricular arrhythmias in these individuals generally produce hemodynamically significant signs or symptoms such as syncope, heart failure, myocardial ischemia or hypotension. These patients have the highest risk of sudden cardiac death and usually the most severe form of underlying cardiac disease. See Morganroth & Bigger at p. 1498. The novel compounds of the present invention are effective, aggressive antiarrhythmic therapy suitable for use in this class of individuals, but with less of some of the undesirable side effects generally heretofore tolerated with conventional antiarrhythmic drugs, out of necessity and the unavailability of a suitable alternative to treat the life-threatening arrhythmias.

As stated above, the novel antiarrhythmic agents of the present invention exhibit less of many of the undesirable side effects associated with many conventional antiarrhythmic therapies. These side effects include, but are not limited to, pulmonary toxicity, cardiac depression, and neurological effects nonspecific to the cardiac tissue.

In addition, the novel compounds of the present invention are antifibrillatory as well as antiarrhythmic; they prevent sudden cardiac death by uniformly prolonging the unexcitable period of the heart during each heartbeat. Conventional therapies exhibit anesthetic and/or cardiac depressive properties which merely make the heart less responsive, not less fibrillatory.

Accordingly, the novel cyclic urea compounds of the present invention are useful in treating cardiac arrhythmias and/or cardiac fibrillation in humans or other mammals. Therefore, the present invention relates to a method for treating a human or other mammal suffering from cardiac arrhythmia and/or cardiac fibrillation which comprises administering to said human or other mammal a safe and effective amount of a pharmaceutical composition comprising from 15–90% of a cyclic urea compound active ingredient, or mixtures thereof, and from 10–85% pharmaceutically-acceptable excipients.

The Examples K–R herein exhibit certain patient situations and illustrate the methods in which pharmaceutical compositions containing the novel cyclic urea compounds of the present invention may be used to treat cardiac arrhythmias and/or fibrillation. It is well within the capabilities of one skilled in the art to vary the non-limiting examples described herein to treat a broad class of individuals suffering from cardiac arrhythmia and/or fibrillation.

The following examples will further serve to illustrate the present invention.

EXAMPLE A

Synthesis of 1-[[[5-(4-Chlorophenyl)-2-furanyl]methylene]amino]-3-[3-dimethylamino)propyl]-2-imidazolidinone Hydrochloride

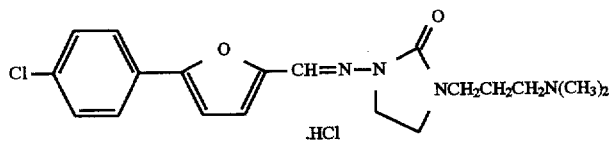

1-[[[5-(4-Chlorophenyl)-2-furanyl]methylene]amino]-3-[3-(dimethylamino)propyl]propyl]-2-imidazolidinone hydrochloride is prepared as described hereinbelow.

I. Synthesis of Dimethylaminopropyl Chloride

Dimethylaminopropyl chloride is prepared by neutralizing the hydrochloride salt with aqueous NaOH in $H_2O$. The neutralized solution is extracted with ether. The ether extract is dried over $MgSO_4$, filtered and concentrated under reduced pressure on a rotary evaporator to a liquid residue.

II. Synthesis of 1-[(Phenylmethylene)amino]-2-imidazolidinone

A stirring solution of 65 g (0.75 mole) of 2-imidazolidinone in 2000 ml of 2N $H_2SO_4$ is cooled to 0° C. A 53 g (0.77 mole) portion of $NaNO_2$ is added portionwise, over a 15 minute period, maintaining the temperature at 0° C. The resulting mixture is stirred at 0° C. for 2 hours. A 108 g (1.65 mole) portion of zinc dust is added portionwise, over a 1 hour period, maintaining the temperature at 0° C. The reaction is stirred at 0° C. for 0.5 hour and then at ambient temperature for 1 hour. The excess zinc is removed by filtration. The filtrate is treated all at once, with a solution of 80 g (0.75 mole) of benzaldehyde, in 400 ml of S.D.A. #32 and the resulting mixture is stirred hours at about 16 to 18 hours at ambient temperature. The solid is collected by filtration, washed with $H_2O$, and air-dried to yield 124 g (87%) of 1-[(phenylmethyl)amino]-2-imidazolidinone.

III. Synthesis of 3-[3-Dimethylamino)propyl]-1-[(phenylmethylene) amino]-2-imidazolidinone A near solution of 9.46 g (0.050 mole) of 1-[(phenylmethylene)amino]-2-imidazolidinone in 125 ml of dimethylformamide is treated portionwise with 2.0 g (0.050 mole) of NaH (60% dispersion in mineral oil) with the temperature rising to 30° C. The reaction is stirred at ambient temperature for 15 minutes with a solid forming. A 100 ml portion of dimethylformamide is added, to aid in stirring, and the mixture is stirred at 80° to 90° C. for 30 minutes. The mixture is cooled to ambient temperature and treated all at once with 12.2 g (0.100 mole) of dimethylaminopropyl chloride (prepared as described in Part I above). The resulting mixture is heated at 80° to 90° C. for 3 hours with near dissolution. The solvent is removed in vacuo. The residual semi-solid is dissolved in $H_2O$ (150 ml), and extracted with ethyl acetate (2×200 ml). The combined extracts are dried over $MgSO_4$ and the solvent is removed in vacuo. The residual solid is washed with ether and air-dried to yield 4.8 g of 3-[3-(dimethylamino)propyl]-1-[(phenylmethylene)amino]-2-imidazolidinone.

IV. Synthesis of 1-[[[5-(4-Chlorophenyl)-2-furanyl]methylene]amino]-3-[3-(dimethylamino)propyl]-2-imidazolidinone hydrochloride A solution of 4.8 g (0.017 mole) of 3-[3-(dimethylamino)propyl]-1-[(phenylmethylene)amino]-2-imidazolidinone (prepared as described in Part III above) in 125 ml of 2N HCl is treated with 1 g of 5% Pd/C (50% $H_2O$) and placed on the Parr reduction apparatus, with the theoretical amount of $H_2$ being absorbed over a 30 minute period. The catalyst is removed by filtration and the solvent is removed in vacuo. The residual oil is dissolved in 100 ml of dimethylformamide and treated all at once with 3.51 g (0.0170 mole) of 5-(4-chlorophenyl)-2-furancarboxaldehyde (prepared as described in U.S. Pat. No. 4,882,354 to Huang et al., (issued Nov. 21, 1989), assigned to Norwich Eaton Pharmaceuticals, Inc., see Example 3, cols. 7 & 8, hereby incorporated by reference herein) with dissolution. A 1.0 g portion of 3 Angstrom molecular sieves is added and the reaction is stirred 16 to 18 hours at ambient temperature. The resulting mixture is heated to reflux with dimethylformamide being added to dissolution. The molecular sieves are removed by filtration and the solvent is removed in vacuo. The residual semi-solid is crystallized by trituration with ether. The solid is recrystallized from S.D.A. #32, (activated charcoal) and dried in a vacuum pistol over refluxing ethyl acetate to yield 2.7 g of 1-[[[5-(4-chlorophenyl)-2-furanyl]methylene]amino]-3-(3-dimethylaminopropyl)-2-imidazolidinone hydrochloride.

EXAMPLE B

Synthesis of 1-[[[5-(4-Chlorophenyl)-2-furanyl]methylene]amino]-3-[4-(4-methyl-1-piperazinyl)butyl]-2-imidazolidinone Dimaleate

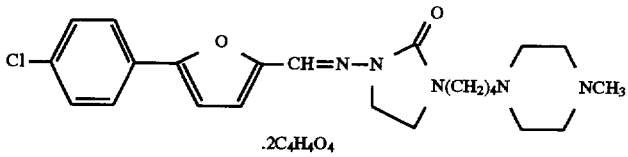

1-[[[5-(4-Chlorophenyl)-2-furanyl]methylene]amino]-3-[4-(4-methyl-1-piperazinyl)butyl]-2-imidolidinone dimaleate is prepared as described hereinbelow.

I. Synthesis of 1-Phenylmethyleneamino-3-(4-chlorobutyl)-2-imidazolidinone

A stirred mixture of 1-phenylmethylenamino-2-imidazolidinone (27.6 g, 0.1458 mole) [prepared as in Example A, Part II] in dimethylformamide (500 ml) is treated portionwise with 60% NaH in mineral oil (5.8 g, 0.1458 mole) over 30 minutes. The resulting mixture is stirred at ambient temperature 30 minutes, then heated at 80°–90° C. for 30 minutes. The resulting thick mixture is cooled to ambient temperature, and 1-bromo-4-chlorobutane (50.0 g, 0.2916 mole, 2 eq) is added in one portion. The mixture is heated at 80°–90° C. After 30 minutes, a near-solution is formed followed, by gradual precipitation of a small amount of solid. The mixture is heated at 80°–90° C. temperature for 3 hours, then stirred at ambient temperature for 18 hours. The mixture is filtered (celite) removing a small amount of insoluble material. The filtrate is concentrated under reduced pressure to an oily residue. This residue is triturated with $H_2O$ giving a solid. The solid is collected and air-dried. This solid is triturated by stirring in anhydrous ether (350 ml) for one hour. The solid is collected and air-dried to give 36.4 g (0.130 mole) of 1-phenylmethyleneamino-3-(4-chlorobutyl)-2-imidazolidinone.

II. Synthesis of 1-Phenylmethyleneamino-3-(4-iodobutyl)-2-imidazolidinone

A stirred mixture of 1-phenylmethyleneamino-3-(4-chlorobutyl)-2-imidazolidinone (36.4 g, 0.1301 mole), acetone (700 ml) and sodium iodide (42.9 g, 0.2862 mole) is heated to reflux which is maintained for 24 hours. The mixture is filtered hot, removing the solid. After cooling, the filtrate is poured into $H_2O$ (2000 ml) and stirred 1 hour. The solid is collected, washed with $H_2O$, and air-dried to give 31.4 g, (0.0845 mole) of 1-phenylmethyleneamino-3-(4-iodobutyl)-2-imidazolidinone.

III. Synthesis of 1-Phenylmethyleneamino-3-[4-(4-methyl-1-piperazinyl)butyl]-2-imidazolidinone A stirred solution of 1-phenylmethyleneamino-3-(4-iodobutyl)-2-imidazolidinone (10.0 g, 0.0269 mole), dimethylformamide (150 ml) and 1-methylpiperazine (6.0 ml, 3.4 g, 0.0539 mole) is heated to reflux. Reflux is maintained for 2.5 hours. The solution is concentrated under reduced pressure to a semi-solid residue. This residue is dissolved in $CHCl_3$ (300 ml), then washed with saturated $NaHC_3$ solution. (3×400 ml), $H_2O$ (2×100 ml) and dried over $MgSO_4$. The filtered solution is concentrated under reduced pressure to an oily residue. This residue is triturated in hexane (300 ml) by stirring. The solid is collected and air-dried to give 8.0 g (0.0233 mole) of 1-phenylmethyleneamino-3-[4-(4-methyl-1-piperazinyl)butyl]-2-imidazolidinone.

IV. Synthesis of 1-[[[5-(4-Chlorophenyl)-2-furanyl]methylene]amino]-3-]4-(4-methyl-1-piperazinyl)butyl]-2-imidazolidinone Dimaleate Salt A mixture of 1-phenylmethyleneamino-3-[4-(4-methyl-1-piperazinyl)butyl]-2-imidazolidinone (3.0 g, 0.0087 mole), 2N HCl (125 ml) and 5% Pd/C (50% $H_2O$) (2.0 g) is subjected to hydrogen on a Parr apparatus at 40 psi at ambient temperature. After 3 hours, 100% of the theoretical $H_2$ uptake is observed. The filtrate is concentrated under reduced pressure to an oily residue. This residue is azeotroped with absolute ethanol (1×25 ml), then concentrated under high vacuum to an oily residue.

A solution of the above residue, dimethylformamide (50 ml) and 5-(4-chlorophenyl)-2-furancarboxaldehyde (prepared as described in U.S. Pat. No. 4,882,354 to Huang et al., assigned to Norwich Eaton Pharmaceuticals, Inc., issued Nov. 21, 1989, see Example 3, cols. 7, 8 hereby incorporated by reference herein) (1.80 g, 0.0087 mole) is stirred at ambient temperature for 17–18 hours. The mixture is concentrated under reduced pressure to a solid residue. This residue is suspended in $H_2O$ (250 ml) then extracted with ethyl acetate (4×75 ml). The aqueous phase is made basic with saturated $NaHCO_3$ solution. This cloudy mixture is extracted with ethyl acetate (3×100 ml). The extract is washed with $H_2O$ (2×50 ml) then dried over $MgSO_4$ (activated charcoal). The filtered solution is concentrated under reduced pressure to a solid residue (1.28 g, 0.0028 mole). This residue is dissolved in absolute ethanol (50 ml), then treated with a solution of maleic acid (0.673 g, 0.0058 mole) dissolved in absolute ethanol (5 ml). The resulting mixture is stirred at ambient temperature for 1 hour. The solid is collected and air-dried. Further drying in vacuo at ambient temperature for 24 hours gave 1.74 g (0.0026 mole) of 1-[[[5-( 4-chlorophenyl)-2-furanyl]methylene]amino]-3-[4-(4-methyl-1-piperazinyl)butyl]-2-imidazolidinone dimaleate salt.

EXAMPLE C

Synthesis of 1-[[[5-(4-Chlorophenyl)-2-furanyl]methylene]amino]-3-[4-(dimethylamino)butyl]-2-imidazolidinone Hydrochloride

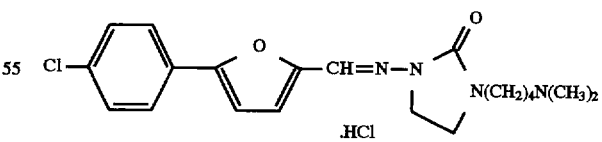

1-[[[5-(4-Chlorophenyl)-2-furanyl]methylene]amino]-3-[4-(dimethylamino)butyl]-2-imidazolidinone hydrochloride is prepared as described hereinbelow:

I. Synthesis of 1-Phenylmethyleneamino-3-[4-(dimethylamino)butyl]-2-imidazolidinone A stirred solution of 1-phenylmethyleneamino-3-(4-iodobutyl)-2-imidazolidinone (prepared as described in Example B, Part II) (7.0 g, 0.0189 mole), dimethylformamide (125 ml), and dimethylamine hydrochloride (6.15 g, 0.075 mole) is heated on a steam bath. Sodium methoxide (4.05 g, 0.075 mole) is added portionwise over approximately 2 hours while heating. After addition, heating is continued 2 hours, then the mixture is cooled to ambient temperature. The mixture is concentrated under reduced pressure to an oily residue. This residue is suspended in saturated $NaHCO_3$ solution. (300 ml) and extracted with $CH_2Cl_2$ (3×100 ml). The $CH_2Cl_2$ extract is washed with $H_2O$ (2×100 ml), then dried over $MgSO_4$. The filtered solution is concentrated under reduced pressure to an oily-liquid residue, which is triturated in hexane (2×100 ml), decanted, then dried in vacuo, giving 4.6 g (0.016 mole) of 1-phenylmethyleneamino-3-[4-(dimethylamino)butyl]-2-imidazolidinone, as a solid.

II. Synthesis of 1-[[[5-(4-Chlorophenyl)-2-furanyl] methylene]amino]-3-[4-dimethylamino)butyl]-2-imidazolidinone Hydrochloride 1-Phenylmethyleneamino-3-[4-(dimethylamino)butyl]-2-imidazolidinone as the solid prepared in Part II above (4.6 g, 0.016 mole) is dissolved in 2N HCl (125 ml). The cloudy solution is immediately extracted with ethyl acetate (2×75 ml). The aqueous phase is treated with 5% Pd/C (50% $H_2O$) (2 g) and subjected to $H_2$ on a Parr apparatus at 40 psi at ambient temperature. After 1 hour additional catalyst (2 g) is added and hydrogenation is resumed. After shaking 15–16 hours, the catalyst is removed by filtration. The filtrate is concentrated under reduced pressure to an oily residue, which is azeotroped with acetone (1×25 ml).

The above residue, dimethylformamide (100 ml) and 5-(4-chlorophenyl)-2-furanylcarboxaldehyde (prepared as described in U.S. Pat. No. 4,882,354 to Huang et al., assigned to Norwich Eaton Pharmaceuticals, Inc., issued Nov. 21, 1989, see Example 3, cols. 7, 8, hereby incorporated by reference herein) (3.30 g, 0.0160 mole) are stirred at ambient temperature for several days. The resulting solution is concentrated under reduced pressure to an oily residue. This residue is dissolved in $H_2O$ (200 ml), then extracted with ethyl acetate (3×100 ml). The aqueous phase is made basic with saturated $NaHCO_3$ solution. This hazy solution is extracted with ethyl acetate (4×100 ml), and the organic extract is dried over $MgSO_4$. The filtered solution is concentrated under reduced pressure to a solid residue. This residue is recrystallized from ethyl acetate/hexane. The collected solid is air-dried, dissolved in absolute ethanol (50 ml) and treated with EtOH/HCl until acidic. After cooling several hours the solid is collected, air-dried, and dried in vacuo at 100° C. for 2 hours to give 1.92 g (0.0045 mole) of 1-[[[5-(4-chlorophenyl)-2-furanyl]-methylene]amino]-3-[4-(dimethylamino)butyl]-2-imidazolidinone hydrochloride.

EXAMPLE D

Synthesis of 1-[[[5-(4-Chlorophenyl)-2-furanyl] methylene]amino]-3-[2-(dimethylamino)ethyl]-1-imidazolidinone Hydrochloride

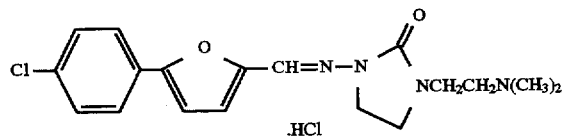

The above compound is prepared as described herein.

I. Synthesis of Dimethylaminoethyl Chloride

A stirred solution of dimethylaminoethyl chloride hydrochloride (36.73 g, 0.26 mole) in water (65 ml) is chilled on an ice bath. The cold reaction mixture is treated dropwise (15 minutes) with a solution of sodium hydroxide (10.6 g, 0.26 mole) in water (90 ml) at such a rate as to maintain a reaction temperature of 10° C. Stirring of the reaction solution is continued for another 15 minutes, and then extraction is conducted with 3×150 ml portions of ether. The extracts are combined and dried over anhydrous $MgSO_4$. The extract mixture is filtered and the filtrate concentrated under reduced pressure to leave a clear oil as dimethylaminoethyl chloride (18.2 g).

II. Synthesis of 1-Phenylmethyleneamino-3-[2-(dimethylamino)ethyl]-2-imidazolidinone A solution of 1-phenylmethyleneamino-2-imidazolidinone (prepared as described in Part II of Example A (14.4 g, 0.076 mole) in dry dimethylformamide (338 ml) is stirred and treated portionwise over a 3 minute period with sodium hydride (60% dispersion in mineral oil) (3.0 g, 0.023 mole). During the addition, a nitrogen sweep is maintained. After the addition is complete, the reaction is heated on a steam bath for 15 minutes and then chilled to ambient temperature. The nitrogen sweep is discontinued and the reaction mixture is treated all at once with dimethylaminoethyl chloride (17.66 g, 0.16 mole), prepared as described in Part I herein. The reaction is stirred at ambient temperature for 15 minutes and then heated at 80° to 90° C. for 3 hours. The reaction is filtered hot, and the filtrate is chilled and concentrated under reduced pressure to leave an oily residue. The residue is treated with 300 ml of water and extracted with 3×300 ml portions of chloroform. The extracts are combined and dried over anhydrous $MgSO_4$. The extract is filtered and the filtrate is concentrated under reduced pressure to leave a tan-colored semi-solid. The semi-solid is triturated with anhydrous ether to give the 1-phenylmethyleneamino-3-[2-(dimethylamino)ethyl]-2-imidazolidinone, weighing 6.17 g.

III. Synthesis of 1-[[[5-(4-Chlorophenyl)-2-furanyl] methylene]- amino]-3-[2-(dimethylamino)ethyl]-2-imidazolidinone Hydrochloride A mixture of 1-phenylmethyleneamino-3-[2-(dimethylamino)ethyl]-2-imidazolidinone, prepared as described in Part II above (6.17 g, 0.023 mole) in 2N HCl (166 ml) is treated with 5% palladium on carbon (50% wet catalyst) (1.3 g). The reaction mixture is reduced on Parr apparatus under hydrogen. The hydrogen uptake stopped after ½ hour with 100% of theoretical uptake observed. The catalyst is removed and the filtrate concentrated under reduced pressure to leave a white residue. The residue is treated with a solution of 5-(4-chlorophenyl)-2-furancarboxaldehyde (prepared as described in U.S. Pat. No. 4,882,354 to Huang et al., assigned to Norwich Eaton Pharmaceuticals, Inc., issued Nov. 21, 1989, see Example 3, cols. 7, 8, hereby incorporated by reference herein) (4.81 g, 0.023 mole) in dry dimethylformamide (137 ml). The reaction is stirred at ambient temperature overnight. The reaction mixture is filtered and washed with anhydrous ether to give 1-[[[5-(4-chlorophenyl)-2-furanyl]methylene]amino]-3-[2-(dimethylamino) ethyl]-2-imidazolidinone hydrochloride.

EXAMPLE E

Preparation of 1-[[[5-(4-Chlorophenyl)-2-furanyl] methylene]amino]-3-[3-(dimethylamino)propyl]-2-imidazolidinone Hydrochloride Oral Tablet An oral tablet containing 1-[[[5-(4-chlorophenyl)-2-furanyl]methylene]amino]-3-[(3-dimethylamino)propyl)]-2-imidazolidinone hydrochloride, (prepared as described in Example A herein), is has the following composition.

| ACTIVE INGREDIENT | |
|---|---|
| 1-[[[5-(4-Chlorophenyl)-2-furanyl]methylene]amino]-3-[3-(dimethylamino)propyl]-2-imidazolidinone hydrochloride | 350 mg |
| EXCIPIENTS | |
| Lactose | 197 mg |
| Sodium Starch Glycolate | 50 mg |
| Pregelatinized Starch | 30 mg |
| Talc | 12 mg |
| Magnesium Stearate | 6 mg |

Ten thousand tablets having the above composition are prepared as described below:

3.50 kg of 1-[[[5-(4-chlorophenyl)-2-furanyl]methylene]amino]-3-[3-(dimethylamino)propyl]-2-imidazolidinone hydrochloride; 1.92 kg of lactose, 0.50 kg of sodium starch glycolate, and 0.30 kg of pregelatinized starch are blended in the Patterson-Kelly blender and then granulated with water using the intensifier bar.

The granulation is next dried on trays in an oven or in a fluid bed dryer.

The granulation is milled through a 12-mesh screen using an oscillator or other suitable mill.

The granulation is blended with 120 g of talc and 60 g of magnesium stearate.

The talc magnesium and granulation mixture is compressed into 440 mg tablets on a suitable tablet machine.

The tablet prepared as described above are given to a patient suffering from cardiac arrhythmia and/or cardiac fibrillation in a suitable dosage regimen.

EXAMPLE F

Preparation of 1-[[[5-(4-Chlorophenyl)-2-furanyl]methylene]amino]-3-[4-(dimethylamino)butyl]-2-imidazolidinone Hydrochloride Oral Tablet An oral tablet containing 1-[[[5-(4-chlorophenyl)-2-furanyl]methylene]amino]-3-[4-(dimethylamino)butyl]-2-imidazolidinone hydrochloride (prepared as described in Example C herein), has the following composition:

| ACTIVE INGREDIENT | |
|---|---|
| 1-[[[5-(4-Chlorophenyl)-2-furanyl]methylene]amino)-3-[4-(dimethylamino)butyl]-2-imidazolidinone hydrochloride | 300 mg |
| EXCIPIENTS | |
| Dibasic Calcium Phosphate | 219 mg |
| Crospovidone | 60 mg |
| Povidone | 12 mg |
| Talc | 6 mg |
| Magnesium Stearate | 3 mg |

Ten thousand tablets having the above composition are prepared as described below:

3.00 kg of 1-[[[5-(4-chlorophenyl)-2-furanyl]methylene]amino]-3-[4-(dimethylamino)butyl]-2-imidazolidinone hydrochloride, 219 kg of dibasic calcium phosphate, 0.60 kg of crospovidone, and 0.12 kg of povidone are blended in a Patterson-Kelly blender and then granulated with water using the intensifier bar.

The granulation is dried on trays in an oven or in a fluid bed dryer. The granulation is next milled through a 12 mesh screen using an oscillator or other suitable mill.

The granulation is blended with 60 g of talc and 30 g of magnesium stearate. Finally, the granulation, talc, and magnesium stearate mixture is compressed into 600 mg tablets on a suitable tablet machine.

A patient suffering from cardiac arrhythmia and/or cardiac fibrillation is given the tablet, prepared as described above, in a suitable dosage regimen.

EXAMPLE G

Preparation of 1-[[[5-(4-Chlorophenyl)-2-furanyl]methylene]amino]-3-[4-(dimethylamino)butyl]-2-imidazolidinone Hydrochloride Oral Capsule An oral capsule containing 1-[[[5-(4-chlorophenyl)-2-furanyl]methylene]amino]-3-[4-(dimethylamino)butyl]-2-imidazolidinone hydrochloride, (prepared as described in Example C herein) has the following composition:

| ACTIVE INGREDIENT | |
|---|---|
| 1-[[[5-(4-Chlorophenyl)-2-furanyl]methylene]amino]-3-[4-(dimethylamino)butyl]-2-imidazolidinone hydrochloride | 300 mg |
| EXCIPIENTS | |
| Lactose | 92 mg |
| Sodium Starch Glycolate | 40 mg |
| Pregelatinized Starch | 25 mg |
| Talc | 12 mg |
| Magnesium Stearate | 3 mg |
| Hard Gelatin Capsule Shell | 1 per capsule |

Ten thousand oral capsules having the above composition are prepared as described below:

3.00 kg of 1-[[[5-(4-chlorophenyl)-2-furanyl]methylene]amino]-3-[4-(dimethylamino)butyl]-2-imidazolidinone hydrochloride, 0.92 kg of lactose, 0.40 kg of sodium starch glycolate, and 0.25 kg of pregelatinized starch are blended in a Patterson-Kelly blender and granulated with water using the intensified bar.

The granulation is dried on trays in an oven or in a fluid bed dryer.

The granulation is milled through a 12-mesh screen using an oscillator or other suitable mill. The granulation is blended with 120 g of talc and 30 g of magnesium stearate.

Finally, 472 mg of granulation, talc, and magnesium stearate mixture is filled into each capsule shell on a suitable capsule filling machine.

A patient suffering from cardiac arrhythmia and/or cardiac fibrillation is given the oral capsule, prepared as described above, in a suitable dosage regimen.

EXAMPLE H

Preparation of 1-[[[5-[4-Chlorophenyl)-2-furanyl]methylene]amino]-3-[3-(dimethylamino)propyl]-2-imidazolidinone hydrochloride Oral Capsule An oral capsule containing 1-[[[5-[4-chlorophenyl)-2-furanyl]methylene]amino]-3-[(3-dimethylamino)propyl]-2-imidazolidinone hydrochloride (prepared as described in Example A herein), has the following composition:

| ACTIVE INGREDIENT | |
|---|---|
| 1-[[[5-[4-Chlorophenyl)-2-furanyl]methylene]amino]-3-[3-(dimethylamino)propyl]-2-imidazolidinone hydrochloride | 175 mg |
| EXCIPIENTS | |
| Microcrystalline Cellulose | 110 mg |
| Crospovidone | 25 mg |
| Povidone | 5 mg |
| Talc | 5 mg |
| Magnesium Stearate | 2 mg |
| Hard Gelatin Capsule Shell | 1 per capsule |

Ten thousand capsules having the above composition are prepared as described below:

1.75 kg of 1-[[[5-(4-chlorophenyl)-2-furanyl]methyleneamino]-3-[3-(dimethylamino)propyl]-2-imidazolidinone hydrochloride, 1.10 kg of microcrystalline cellulose, 0.25 kg of crospovidone, and 0.05 kg of povidone are blended in a Patterson-Kelly or other suitable blender and then granulated with water using the intensifier bar.

The granulation is dried on trays in an oven or a fluid bed dryer. The granulation is milled through a 12 mesh screen using an oscillator or other suitable mill. The granulation is blended with 50 g of talc and 20 g of magnesium stearate.

322 mg of the granulation, talc, and magnesium stearate mixture is filled into each capsule shell on a suitable capsule filling machine.

The oral capsule prepared as described above is given to a patient suffering from cardiac arrhythmia and/or cardiac fibrillation in a suitable dosage regimen.

EXAMPLE I

Preparation of 1-[[5-(4-Chlorophenyl)-2-furanyl]methylene]amino]-3-[4-(dimethylamino)butyl]-2-imidazolidinone Hydrochloride Lyophilized Injection A solution suitable for use as an intravenous (I.V.) injection consisting of 1-[[[5-(4-chlorophenyl)-2-furanyl]methylene]amino]-3-[4-(dimethylamino)butyl]-2-imidazolidinone hydrochloride, (prepared as described in Example C herein), has the following composition:

| ACTIVE INGREDIENT | |
|---|---|
| 1-[[[5-(4-Chlorophenyl)-2-furanyl]methylene]amino]-3-[4-(dimethylamino)butyl]-2-imidazolidinone hydrochloride | 400 mg |
| EXCIPIENTS | |
| Mannitol | 500 mg |
| Citric Acid/Sodium Citrate | -quantity sufficient to adjust pH to 5.5–6.5 |

The method to make 1,000 vials of the above solution for I.V. injection is as described hereinbelow.

400 g of 1-[[[5-(4-chlorophenyl)-2-furanyl]methylene]amino]-3-[4-(dimethylamino)butyl]-2-imidazolidinone hydrochloride, 500 g mannitol, and sufficient sodium citrate and/or citric acid to make a pH solution are dissolved in 10.0 liters of sterile water for injection.

The resulting solution is aseptically filtered through a 0.2 micron filter and filled into vials in the amount of 10 ml per vial.

The vials are loaded into a lyophilizer, frozen, dried and stoppered. The lyophilized product is diluted with 10 ml of sterile water immediately prior to injection.

A patient suffering from cardiac arrhythmia and/or cardiac fibrillation is given an injection, prepared as described above, in a suitable dosage regimen.

EXAMPLE J

Any of the compounds prepared in Examples A–D herein can be substituted as the active ingredient in any of the dosage forms prepared in Examples E–I herein.

EXAMPLE K

A 57-year-old white male is found unconscious and without palpable pulse at home. A family member initiates cardiopulmonary resuscitation. The first rhythm documented by the rescue squad is ventricular fibrillation. The patient is successfully resuscitated.

The patient had a myocardial infarction three years ago, and has had stable angina since.

During the ensuing hospitalization, the patient is found not to have had a myocardial infarction. Monomorphic sustained ventricular tachyarrhythmia is induced by programmed electrical stimulation.

The patient's cardiologist prescribes 1-[[[5-(4-chlorophenyl)-2-furanyl]methylene]-amino]-3-[3-(dimethylamino)propyl]-2-imidazolidinone hydrochloride at an oral dose of 350 mg, twice a day, after meals. After four days of therapy, the arrhythmia is not inducible at a repeat programmed electrical stimulation study. The patient has no further episodes of cardiac arrest over the next 2 years, and treatment continues.

EXAMPLE L

A 65-year-old black male has a syncopal spell preceded by sensations of palpitations. Over the preceding several months, the patient had experienced frequent palpitations, once with a near-fainting spell. He has a history of hypertensive cardiovascular disease, diabetes, remote myocardial infarction, and obesity.

Sustained monomorphic ventricular tachycardia is induced by programmed electrical stimulation. The patient's cardiologist prescribes 1-[[[5-(4-chlorophenyl)-2-furanyl]methylene]amino]-3-[[4-dimethylamino)butyl]-2-imidazolidinone hydrochloride, orally, at a dose of 350, once a day, with a meal. After several days of therapy, the arrhythmia is noninducible on repeat programmed electrical stimulation. There are no further episodes of syncope or presyncope over the next three years of observation.

EXAMPLE M

A 58-year-old female Oriental patient with a cardiomyopathy presents with recurrent syncope. Her ejection fraction is 35%. Programmed electrical stimulation (PES) induces poorly tolerated sustained ventricular tachyarrhythmia unresponsive to three different antiarrhythmic drugs. A fourth drug, moricizine, reduces the rate of the tachyarrhythmia and is continued, but the tachyarrhythmia still induces hypotension. She undergoes implantation of an automatic implantable cardioverter-defibrillator (AICD).

The defibrillator discharges twice in the year after implantation of the AICD. The device's monitor records sustained ventricular tachyarrhythmia at the times of defibrillation. After the second discharge, the patient is hospitalized. Sustained monomorphic ventricular tachyarrhythmia is induced at PES. Moricizine is discontinued and 1-[[[5-(4-chlorophenyl)-2-furanyl]methylene]-amino]-3-[3-(dimethylamino)propyl]-2-imidazolidinone hydrochloride at an oral dose of 350 mg, twice a day, after meals, is started by the patient's cardiologist.

At repeat PES several days later, the arrhythmia is not inducible and the defibrillation threshold is unchanged. Over the subsequent year of observation, no further discharges are experienced.

EXAMPLE N

A 35-year-old female presents with a 15-year history of frequent (2/month) spells of rapid heartbeat, lasting several hours, associated with dizziness and fatigue. These spells cause her to miss time from work.

A transtelephonic event monitor demonstrates paroxysmal supraventricular tachycardia. The patient's physician prescribes 1-[[[5-(4-chlorophenyl)-2-furanyl]methylene]amino]-3-[3-(dimethylamino)propyl]-2-imidazolidinone hydrochloride at a dose of 175 mg, once a day, after a meal.

Over the subsequent year of observation, the frequency of these spells decreases to one every other month, with marked improvement in her attendance record at work.

EXAMPLE O

A 75-year-old male who has a fifty pack-year history of smoking has known episodes of atrial fibrillation documented by transtelephonic monitoring, at the rate of three per month, while on therapy with digoxin and quinidine. These spells sometimes last over eight hours and prevent the patient's pursuit of his normal daily activities, such as gardening, due to weakness.

The patient's physician switches the patient from quinidine to 1-[[[5-(4-chlorophenyl)-2-furanyl]methylene]amino]-3-[3-(dimethylamino)propyl]-2-imidazolidinone hydrochloride orally at a dose of 175 mg, once a day, after a meal. The frequency of spells decreases to one a month over the subsequent four months of observation.

EXAMPLE P

A 40-year-old Caucasian male has a several year history of frequent palpitations. The patient experiences anxiety and shortness of breath at the time of the palpitations, and has become preoccupied by a fear of death. Extensive evaluations have demonstrated an absence of structural heart disease. Holter monitoring has shown 2500 PVCs per day, unifocal, with 50 couplets per day. Neither reassurance, nor subsequent therapy with propranolol, have been effective.

The physician prescribes 1-[[[5-(4-chlorophenyl)-2-furanyl]methylene]amino]-3-[4-(4-methyl-1-piperazinyl)-butyl]-2-imidazolidinone dimaleate at an oral dose of 350 mg, once a day, after a meal.

The frequency of the palpitations decreases and the associated anxiety and shortness of breath are relieved. Holter monitoring now shows 250 PVCs per day and no repetitive forms. The preoccupation with death resolves over several months. The patient is monitored closely, and continues to do well over the subsequent five years.

EXAMPLE Q

A fifty-eight-year old black male with a ten year history of non-insulin dependent diabetes mellitus and a cholesterol level exceeding 300 mg/dl has a myocardial infarction. Two weeks after the infarction, he is asymptomatic with the exception of dyspnea on exertion. His ejection fraction is 29%, and 24 hour Holter monitoring reveals 50 unifocal PVCs per hour, occasional couplets, and one five beat run of ventricular tachyarrhythmia. His cardiologist prescribes 1-[[[5-(4-chlorophenyl)-2-furanyl]methylene]amino]-3-[4-(dimethylamino)butyl]-2-imidazolidinone hydrochloride at an oral dose of 300 mg after meals. Repeat Holter monitoring shows abolition of all repetitive forms and an average of 9 PVCs per hour. The patient does well over the next three years of follow up.

EXAMPLE R

Any of the dosage forms prepared as described in Examples E–I herein, utilizing any of the active ingredients prepared in Examples A–D herein, may be used to treat the individuals described in Examples K–Q herein, in a suitable dosage regimen.

What is claimed is:

1. A cyclic urea compound which has the structure:

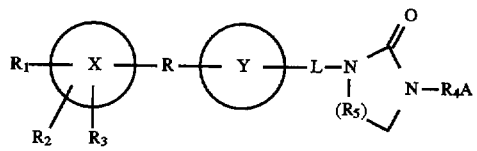

wherein a) X is a saturated or unsaturated, substituted or unsubstituted 6-membered carbocycle;

b) R is a covalent bond;

c) Y is a saturated or unsaturated, substituted or unsubstituted 5-membered heterocycle, wherein said heterocycle has one or two heteroatoms selected from O, S or N;

d) $R_1$, $R_2$, and $R_3$ are substituents on the X moiety and are independently selected from the group consisting of H, Cl, F, Br, $NH_2$, $CF_3$, OH, $SO_3H$, $CH_3$, $SO_2$, NH, COOH, alkoxy, alkoxycarbonyl, alkyl, hydroxyalkyl, carboxyalkyl, amino alkyl, acylamino, and acyloxy;

e) L is a linking moiety and is selected from the group consisting of alkylamino, alkenylamino, alkylimino, alkenylimino, and acylamino, wherein the carbon-containing end of L is bound, through R, at X; and wherein the nitrogen atom of L is bound to the nitrogen atom at the 3-position of the cyclic urethane ring moiety;

f) $R_4$ is selected from the group consisting of alkyl, alkenyl, alkynyl, alkylacyl, and heteroalkyl;

g) A is a substituted or unsubstituted; saturated or unsaturated, straight-chain or branched $C_1$–$C_8$ heteroalkyl; or a substituted or unsubstituted, saturated or unsaturated, heterocycle having 5-, 6- or 7-members and one or two heteroatoms selected from O, N or S; and heteroalkyl A and heterocycle A have at least one nitrogen atom, which nitrogen atom is adjacent to $R_4$; and h) $R_5$ is a substituted or unsubstituted $C_1$ alkyl;

and the pharmaceutically-acceptable salts and esters thereof.

2. A cyclic urea compound according to claim 1 having the structure:

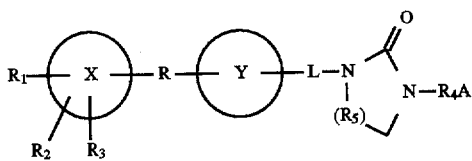

wherein
a) X is a saturated or unsaturated, substituted or unsubstituted phenyl;
b) R is a covalent bond;
c) Y is a furanyl;
d) $R_1$, $R_2$, and $R_3$ are substituents on the X moiety and are independently selected from the group consisting of H, Cl, F, Br, $NH_2$, $CF_3$, OH, $SO_3H$, $CH_3$, $SO_2$, NH, COOH, alkoxy, alkoxycarbonyl, alkyl, hydroxyalkyl, carboxyalkyl, amino alkyl, acylamino, and acyloxy;
e) L is a linking moiety and is selected from the group consisting of alkylamino, alkenylamino, alkylimino, alkenylimino, and acylamino, wherein the carbon-containing end of L is bound, through R, at X; and wherein the nitrogen atom of L is bound to the nitrogen atom at the 3-position of the cyclic urethane ring moiety;
f) $R_4$ is selected from the group consisting of alkyl, alkenyl, alkynyl, alkylacyl, and heteroalkyl;
g) A is a substituted or unsubstituted; saturated or unsaturated, straight-chain or branched $C_1$–$C_8$ heteroalkyl; or a substituted or unsubstituted, saturated or unsaturated, heterocycle having 5-, 6- or 7-members and one or two heteroatoms selected from O, N or S; and heteroalkyl A and heterocycle A have at least one nitrogen atom, which nitrogen atom is adjacent to $R_4$; and
h) $R_5$ is a substituted or unsubstituted $C_1$ alkyl;
and the pharmaceutically-acceptable salts and esters thereof.

3. A cyclic urea compound having the following structure:

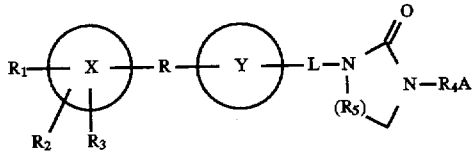

wherein
a) X is phenyl, pyridinyl, thienyl, pyrimidinyl, furanyl, cyclohexyl, oxazolyl, naphthyl, and quinolinyl;
b) R is nil or a covalent bond;
c) Y is phenyl, pyridinyl, thienyl, pyrimidinyl, furanyl, cyclohexyl, oxazolyl, naphthyl, and quinolinyl;
d) $R_1$, $R_2$, and $R_3$ are substituents on the X moiety and are independently selected from the group consisting of H, Cl, F, Br, $NH_2$, $CF_3$, OH, $SO_3H$, $CH_3$, $SO_2$, NH, COOH, alkoxy, alkoxycarbonyl, alkyl, hydroxyalkyl, carboxyalkyl, aminoalkyl, acylamino, and acyloxy;
e) L is a linking moiety and is selected from the group consisting of alkylamino, alkenylamino, alkenylimino, alkylimino, and acylamino, wherein the nitrogen atom thereof is bound to the nitrogen atom at the 1-position of the cyclic urea ring moiety;
f) $R_4$ is selected from the group consisting of alkyl, alkenyl, alkynyl, alkyl, alkylacyl, and heteroalkyl;
g) A is a substituted or unsubstituted; saturated or unsaturated, straight-chain or branched $C_1$–$C_8$ heteroalkyl; or a substituted or unsubstituted, saturated or unsaturated, heterocycle having 6- or 7-members and one or two heteroatoms selected from N or S; and may not have an oxygen atom; and heteroalkyl A and heterocycle A has at least one nitrogen atom, and said nitrogen atom is adjacent to $R_4$; and h) $R_5$ is a substituted or unsubstituted $C_1$ alkyl; and the pharmaceutically-acceptable salts and esters thereof.

4. A cyclic urea compound according to claim 1 having the following structure:

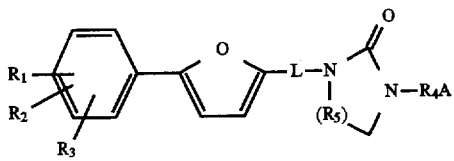

wherein
a) $R_1$, $R_2$, and $R_3$ are independently selected from the group consisting of H, Cl, F, Br, $NH_2$, $CF_3$, OH, $SO_3H$, $CH_3SO_2NH$, COOH, alkoxy, alkoxycarbonyl, alkyl, hydroxyalkyl, carboxyalkyl, aminoalkyl, acyloxy, and acylamino;
b) L is a linking moiety and is selected from the group consisting of alkylamino, alkenylamino, alkenylimino, alkylimino, and acylamino; wherein the carbon-containing end of L is bound to the X-R-Y ring system at Y; and wherein the nitrogen atom of L is bound to the nitrogen atom at the 3-position of the cyclic urethane ring moiety;
c) $R_4$ is selected from the group consisting of alkyl, alkenyl, alkynyl, alkylacyl, and heteroalkyl;
d) A is selected from the group consisting of dimethylamino; diethylamino; bis-2-hydroxy-ethylamino; bis-[(1-methy)ethyl]amino; N-benzyl-N-methylamino; N-(2-hydroxyethyl)-N-methylamino; N-[(1-methyl)ethyl]-N-[2-hydroxy-2-[(4-methanesulfonyl-amino)phenyl]ethyl]amino; 4-phenyl-1-piperazinyl; 4(-2-hydroxyethyl)-1-piperazinyl; 4-[(2-methyl)propyl]-1-piperazinyl; 4-[(2-methyl) propyl]-1piperazinyl; 4-hexyl-1-piperazinyl; 4-benzyl-1-piprazinyl; 1-piperazinyl; 4-hydroxy-1-piprazinyl; 1-piperazxinyl; 4-hydroxy-1-piperidinyl; 4-methyl-1-piperazinyl; 4-n-butyl-1-piperazinyl; 4-ethyl-1-piperazinyl, 3-(4-methyl)-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; 4-methyl-N-phenylamino; 1-imidazolyl,; 4-(2-methylphenyl)-1-piperazinyl; 4-(4-methanesulfonylamino phenyl)-1-9-erazinyl; N-morpholinyl; N-thiomorpholinyl; 4-oxo-1-piperidinyl; 2-(t-butoxycarbonyl)-1-pyridinyl; pyrrolidinyl; 4-4-acetylphenyl)-1-piperazinyl; hexahydro-1H-azepin-1-yl;
e) $R_5$ is a substituted or unsubstituted $C_1$ alkyl;
and the pharmaceutically-acceptable salts and esters thereof.

5. A cyclic urea compound according to claim 1 having the following structure:

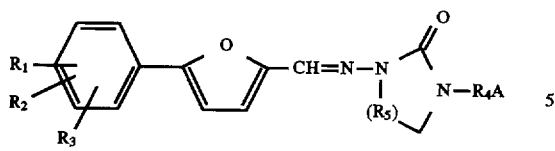

wherein a) $R_1$, $R_2$, and $R_3$ are independently selected from the group consisting of H, Cl, F, Br, $NH_2$, $CF_3$, OH, $SO_3H$, $CH_3SO_2NH$, COOH, alkoxy, alkoxycarbonyl, alkyl, hydroxyalkyl, carboxyalkyl, aminoalkyl, acyloxy, and acylamino;

b) $R_4$ is selected from the group consisting of alkyl, alkenyl, alkynyl, alkylacyl, and heteroalkyl;

c) A is selected from the group consisting of dimethylamino; diethylamino; bis-2-hydroxy-ethylamino; bis-[(1-methy) ethyl]amino; N-benzyl-N-methylamino; N-(2-hydroxyethyl)-N-methylamino; N-[(1-methyl) ethyl]-N-[2-hydroxy-2-[(4-methanesulfonyl-amino) phenyl]ethyl]amino; 4-phenyl-1-piperazinyl; 4(-2-hydroxyethyl)-1-piperazinyl; 4-[(2-methyl)propyl]-1-piperazinyl; 4-[(2-methyl) propyl]-1-piperazinyl; 4-hexyl-1-piperazinyl; 4-benzyl-1-piprazinyl; 1-piperazinyl; 4-hydroxy-1-piprazinyl; 1-piperazxinyl; 4-hydroxy-1-piperidinyl; 4-methyl-1-piperazinyl; 4-n-butyl-1-piperazinyl; 4-ethyl-1-piperazinyl, 3-(4-methyl)-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; 4-methyl-N-phenylamino; 1-imidazolyl,; 4-(2-methylphenyl)-1-piperazinyl; 4-(4-methanesulfonylamino phenyl)-1-9-erazinyl; N-morpholinyl; N-thiomorpholinyl; 4-oxo-1-piperidinyl; 2-(t-butoxycarbonyl)-1-pyridinyl; pyrrolidinyl; 4-4-acetylphenyl)-1-piperazinyl; hexahydro-1H-azepin-1-yl;

d) $R_5$ is a substituted or unsubstituted $C_1$ alkyl;

and the pharmaceutically-acceptable salts and esters thereof.

6. A cyclic urea compound having the following structure:

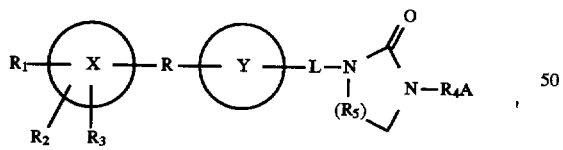

wherein a) wherein the "X-R-Y" portion of the structure is selected from one of the following:

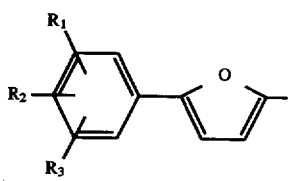

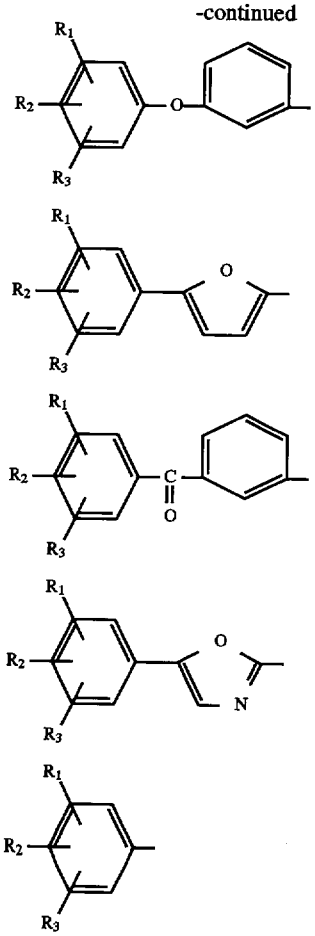

b) wherein $R_1$, $R_2$, and $R_3$ are independently selected from the group consisting of H, Cl, F, Br, $NH_2$, $CF_3$, OH, $SO_3H$, $CH_3SO_2NH$, COOH, alkoxy, alkoxycarbonyl, alkyl, hydroxyalkyl, carboxyalkyl, aminoalkyl, acyloxy, and acylamino;

c) L is a linking moiety and is selected from the group consisting alkylamino, alkenylamino, alkenylimino, alkylimino, and acylamino; wherein the nitrogen atom thereof is bound to the nitrogen atom at the 1-position of the cyclic urea ring moiety;

d) wherein $R_4$ is selected from the group consisting of alkenyl, alkynyl, alkylacyl, and heteroalkyl;

e) $R_5$ is a substituted or unsubstituted $C_1$ alkyl; and f) wherein the A portion of the structure is selected from one of the following:

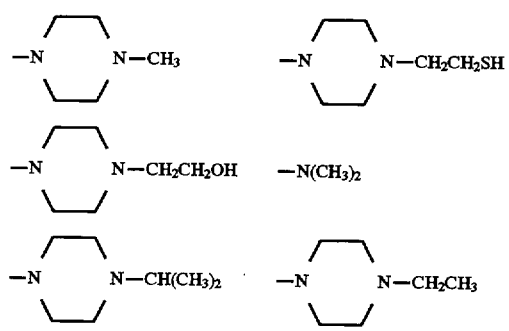

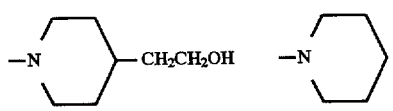

and the pharmaceutically-acceptable salts and esters thereof.

7. A cyclic urea compound having the following structure:

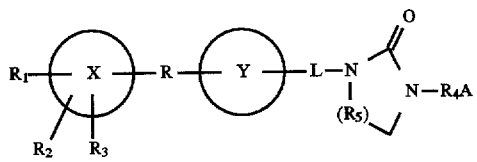

a) wherein the "X-R-Y" portion of the structure is selected from one of the following:

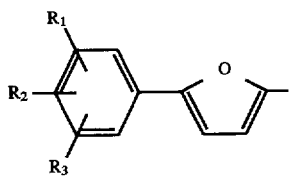

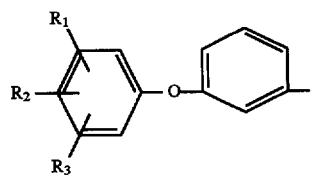

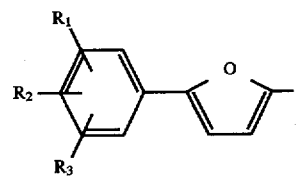

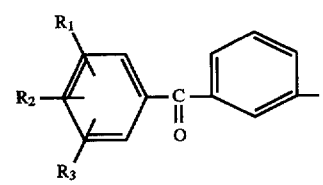

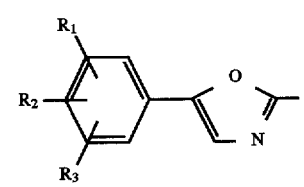

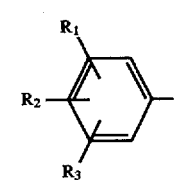

b) wherein $R_1$, $R_2$, and $R_3$ are independently selected from the group consisting of H, Cl, F, Br, $NH_2$, $CF_3$, OH, $SO_3H$, $CH_3SO_2NH$, COOH, alkoxy, alkoxycarbonyl, alkyl, hydroxyalkyl, carboxyalkyl, aminoalkyl, acyloxy, and acylamino;

c) wherein $R_4$ is selected from the group consisting of alkenyl, alkynyl, alkylacyl, and heteroalkyl;

d) $R_5$ is a substituted or unsubstituted $C_1$ alkyl; and e) wherein the A portion of the structure is selected from one of the following:

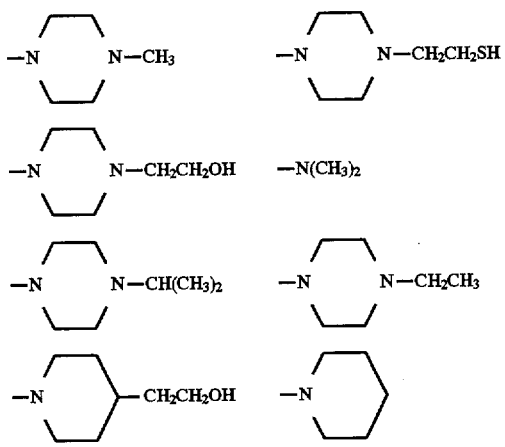

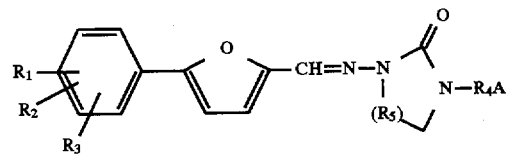

and the pharmaceutically-acceptable salts and esters thereof.

8. A cyclic urea compound having the general structure:

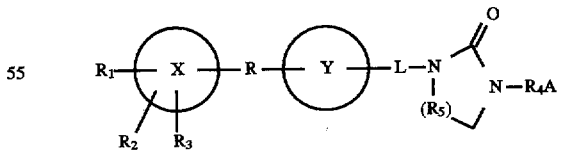

wherein a) $R_1$, $R_2$, and $R_3$ are independently selected from the group consisting of H, Cl, F, Br, $NH_2$, $CF_3$, OH, $SO_3H$, $CH_3SO_2NH$, COOH, alkoxy, alkoxycarbonyl, alkyl, hydroxyalkyl, carboxyalkyl, aminoalkyl, acyloxy and acylamino;

b) $R_4$ is selected from a group consisting of an alkyl, alkenyl, alkynyl, alkylacyl, and heteroalkyl;

c) A is a substituted or unsubstituted, saturated or unsaturated, straight-chain or branched $C_1$–$C_8$ heteroalkyl or a substituted or unsubstituted, saturated or unsaturated heterocycle having 5-, 6-, or 7-members; wherein said heterocycle has one or more heteroatoms selected from nitrogen, sulfur, or oxygen; and d) $R_5$ is a substituted or unsubstituted $C_1$ alkyl;

and the pharmaceutically-acceptable salts and esters thereof.

9. A cyclic urea compound having the following structure:

wherein a) the "X-R-Y" portion of the structure is selected from the group consisting of 2-acetoxy-5-chlorophenyl; 3-hydroxy-5-hydroxymethyl-2-methyl-4-pyridinyl; 2-thienyl; 4-pyrimidinyl; 5-methoxycarbonyl-2-furanyl; cyclohexyl; 5-chloro-2-hydroxyphenyl; 5-chloro-2-methoxyphenyl; 2-methanesulfonylaminophenyl; 3-aminophenyl;

2-methoxyphenyl; 5-ethyl-2-furanyl; 3-methoxyphenyl; 2-aminophenyl; 2-furanyl; 3,5-dimethyl-4-hydroxyphenyl; 5-acetyloxymethyl-2-furanyl; 5-(4-carboxyphenyl)-2-furanyl; 5-(4-methanesulfonylphenyl)-2-furanyl; 5-(3,4-dimethoxyphenyl)-2-furanyl; 5-(4-methanesulfonylaminophenyl)-2-furanyl; 5-(4-bromophenyl)-2-oxazolyl; 5-(4-methoxyphenyl)-2-furanyl; 5-(1-cyclohexen-1-yl)-2-furanyl; 5-cyclohexyl-2-furanyl; 5-(3-trifluoromethylphenyl)-2-furanyl; 5-(4-methylphenyl)-2-furanyl; 2-(4-chlorophenyl)-3-furanyl; 5-(4-chlorophenyl)-2-furanyl; 5-(4-fluorophenyl)-2-furanyl; 2-benzyloxy-5-chlorophenyl; 4-benzyloxyphenyl; 3-(4-t-butylphenyloxy)phenyl; 3-benzoyl-2,4-dichlorophenyl; 2-chloro-3-benzyloxyphenyl; 3-(4-chlorophenoxyl)phenyl; 1H-indol-3-yl; 2-fluorenyl; 2-naphthyl; 2-hydroxy-1-naphthyl; 2-quinolinyl; and 5-chloro-2-benzofuranyl;

b) L is a linking moiety and is selected from the group consisting of alkylamino, alkenylamino, alkenylimino, alkylimino, and acylamino; wherein the nitrogen atom thereof is bound to the nitrogen atom at the 1-position of the cyclic urea ring moiety;

c) $R_4$ is selected from the group consisting of alkenyl, alkynyl, alkylacyl, and heteroalkyl;

d) A is selected from the group consisting of dimethylamino; diethylamino; bis-2-hydroxy-ethylamino; bis-[(1-methy)ethyl]amino; N-benzyl-N-methylamino; N-(2-hydroxyethyl)-N-methylamino; N-[(1-methyl)ethyl]-2-hydroxy-2-[(4-methanesulfonyl-amino)phenyl]ethyl]amino; 4-phenyl-1-piperazinyl; 4(-2-hydroxyethyl)-1-piperazinyl; 4-[(2-methyl)propyl]-1-piperazinyl; 4-[(2-methyl)propyl]-1-piperazinyl; 4-hexyl-1-piperazinyl; 4-benzyl-1-piprazinyl; 1-piperazinyl; 4-hydroxy-1-piprazinyl; 1-piperazxinyl; 4-hydroxy-1-piperidinyl; 4-methyl-1-piperazinyl; piperazinyl; 4-n-butyl-1-piperazinyl; 4-ethyl-1-piperazinyl, 3-(4-methyl)-1-piperazinyl)-3-oxopropyl; 4-phenyl-1-piperazinyl; N-(2-pyridinyl)-1-piperazinyl; N-(2-pyrimidinyl)-1-piperazinyl; 4-(4-methoxyphenyl)-1-piperazinyl; 4-acetyl-1-piperazinyl; piperazinyl; 4-methyl-N-phenylamino; 1-imidazolyl,; 4-(2-methylphenyl)-1-piperazinyl; 4-(4-methanesulfonylamino phenyl)-1-9-erazinyl; N-morpholinyl; N-thiomorpholinyl; 4-oxo-1-piperidinyl; 2-(t-butoxycarbonyl)-1-pyrrolidinyl; pyrrolidinyl; 4-4-acetylphenyl)-1-piperazinyl; hexahydro-1H-azepin-1-yl.

10. A cyclic urea compound having the following structure:

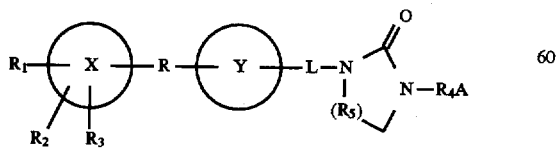

(a) wherein the "X-R-Y" portion of the structure is selected from one of the following:

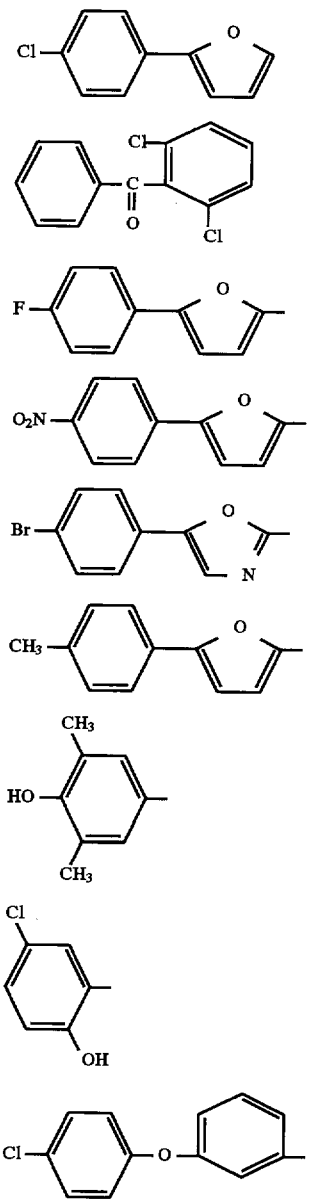

(b) L is a linking moiety and is selected from the group consisting of alkylamino, alkenylamino, alkenylimino, alkylimino, and acylamino; wherein the nitrogen atom thereof is bound to the nitrogen atom at the 1-position of the cyclic urea ring moiety;

(c) wherein $R_4$ is selected from the group consisting of alkenyl, alkynyl, alkylacyl, and heteroalkyl;

(d) wherein the A portion of the structure is selected from one of the following:

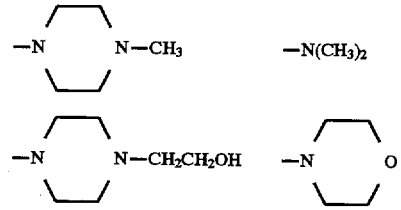

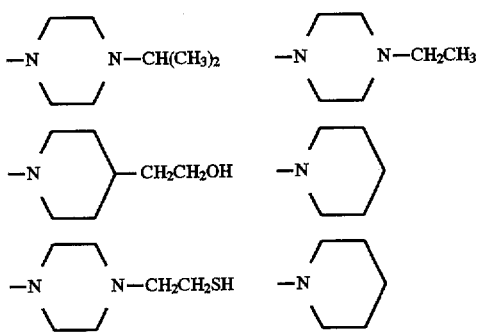

and the pharmaceutically acceptable salts and esters thereof.

11. A compound according to claim 1 wherein X is unsubstituted and $R_1$, $R_2$, and $R_3$ are hydrogen.

12. A compound according to claim 11 wherein $R_1$, $R_2$, and $R_3$ are independently selected from the group consisting of hydrogen, Cl, F, Br, $CH_3$, and OH.

13. A compound according claim 1 wherein Y is a 5-membered heterocycle.

14. A compound according to claim 1 wherein R is adjacent to X at the 1-position of X, and to Y at the 5-position of Y.

15. A compound according to claim 14 wherein Y is connected to the carbon-containing end of L at the 2-position of Y.

16. A compound according to claim 13 wherein a heteroatom of Y is oxygen at the 1-position of said heterocycle.

17. A compound according to claim 16 wherein one of $R_1$, $R_2$, or $R_3$ is Cl, F, or Br and two of $R_1$, $R_2$ or $R_3$ are H.

18. A compound selected from the group consisting of 1-[[[5-(4-(chlorophenyl)-2-furanyl]methylene]amino]-3-[3-(dimethylamino)propyl]-2-imidazolidinone; 1-[[[5-(4-chlorophenyl)-2-furanyl]methylene]amino]-3-[4-(dimethylamino)butyl]-2-imidazolidinone; 1-[[[5-(4-(chlorophenyl)-2-furanyl]methylene]amino]-3-[4-(4-methyl-1-piperazinyl)butyl]-2-imidazolidinone; 1-[[[5-(4-chlorophenyl)-2-furanyl]methylene]amino]-3-[2-(dimethylamino)ethyl]-2-imidazolidinone; 1-[[[3-(4-chlorophenoxy)phenyl]methylene]amino]-3-[3-(dimethylamino)propyl]-2-imidazolidinone; 1-[[5-chloro-2-benzofuranyl)methylene]amino]-3-[3-(dimethylamino)propyl]-2-imidazolidinone; 1-[[3-benzoyl-2,4-dichlorophenyl)methylene]amino]-3-[3-(dimethylamino)propyl]-2-imidazolidinone; 1-[[[5-(4-chlorophenyl)-2-furanyl]methylene]amino]-3-[3-(dimethylamino)propyl] tetrahydro-2-(1 H)pyrimidinone; 1-[[[5-(4-chlorophenyl)-2-furanyl]methylene]amino]-3-[4-[4-(2-hydroxyethyl)-1-piperazinyl]butyl]-2-imidazolidinone; 1-[[[5-(4-chlorophenyl)-2-furanyl]methylene]amino]-3-[3-(4-methyl-1-piperazinyl)propyl]-2-imidazolidinone; 1-[[(cyclohexyl)methylene]amino]-3-[3-(dimethylamino)propyl]-2-imidazolidinone, and the pharmaceutically acceptable hydrochloride and maleate salts thereof.

19. A compound according to claim 1 wherein X is substituted with two or more substituents selected from the group consisting of Cl, OH, methoxy, methyl, and benzoyl.

20. A compound according to claim 1 wherein L is selected from the group consisting of alkylimino, alkylamino, and alkenylimino.

21. A compound according to claim 1 wherein $R_4$ is a $C_3$–$C_6$alkyl.

22. A compound according to claim 1 wherein $R_4$ is a substituted alkyl.

23. A compound according to claim 1 wherein A is a heteroalkyl.

24. A pharmaceutical composition is comprised of a safe and effective amount of from 15 to 90% of a cyclic urea compound of claim 1, or mixtures thereof, and from 10 to 85% pharmaceutically-acceptable excipients.

25. A pharmaceutical composition according to claim 24, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

26. A pharmaceutical composition according to claim 6 comprised of from 15–95% of the cyclic urea active ingredient; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

27. A method of treatment for humans or other mammals afflicted with cardiac arrhythmias and/or cardiac fibrillation comprised of administering to said human or other mammal a safe and effective amount of the pharmaceutical composition of claim 6.

28. A pharmaceutical composition for the treatment of cardiac arrhythmia or cardiac fibrillation comprised of from 15 to 90% of a cyclic urea compound of claim 1, or any mixtures thereof, and from 10 to 85% pharmaceutically-acceptable excipients.

29. A pharmaceutical composition for the treatment of cardiac arrhythmia or cardiac fibrillation comprised of from 15 to 90% of a cyclic urea compound of claim 2, or any mixtures thereof, and from 10 to 85% pharmaceutically-acceptable excipients.

30. A pharmaceutical composition for the treatment of cardiac arrhythmia or cardiac fibrillation comprised of from 15 to 90% of a cyclic urea compound of claim 3, or any mixtures thereof, and from 10 to 85% pharmaceutically-acceptable excipients.

31. A pharmaceutical composition for the treatment of cardiac arrhythmia or cardiac fibrillation comprised of from 15 to 90% of a cyclic urea compound of claim 4 or any mixtures thereof, and from 10 to 85% pharmaceutically-acceptable excipients.

32. A pharmaceutical composition for the treatment of cardiac arrhythmia or cardiac fibrillation comprised of from 15 to 90% of a cyclic urea compound of claim 5, or any mixtures thereof, and from 10 to 85% pharmaceutically-acceptable excipients.

33. A pharmaceutical composition for the treatment of cardiac arrhythmia or cardiac fibrillation comprised of from 15 to 90% of a cyclic urea compound of claim 6, or any mixtures thereof, and from 10 to 85% pharmaceutically-acceptable excipients.

34. A pharmaceutical composition for the treatment of cardiac arrhythmia or cardiac fibrillation comprised of from 15 to 90% of a cyclic urea compound of claim 7, or any mixtures thereof, and from 10 to 85% pharmaceutically-acceptable excipients.

35. A method of treatment for humans or other mammals afflicted with cardiac arrhythmias and/or cardiac fibrillation comprised of administering to said human or other mammal a pharmaceutical composition comprising from 15 to 90% of a cyclic urea compound according to claim 18, pharmaceutically-acceptable salt and esters thereof, or mixtures thereof.

36. A method of treatment for humans or other mammals afflicted with cardiac arrhythmias and/or cardiac fibrillation comprised of administering to said human or other mammal a pharmaceutical composition comprising from 15 to 90% of a cyclic urea compound according to claim 9, pharmaceutically-acceptable salt and esters thereof, or mixtures thereof.

37. A method of treatment for humans or other mammals afflicted with cardiac arrhythmias and/or cardiac fibrillation comprised of administering to said human or other mammal a pharmaceutical composition comprising from 15 to 90% of a cyclic urea compound according to claim 10, pharmaceutically-acceptable salt and esters thereof, or mixtures thereof.

* * * * *